United States Patent [19]

Yamaguchi et al.

[11] Patent Number: 5,126,937
[45] Date of Patent: Jun. 30, 1992

[54] BIOLOGICAL INFORMATION MEASUREMENT APPARATUS

[75] Inventors: Shuichiro Yamaguchi, Fuji; Norihiko Ushizawa, Fujinomiya; Norio Daikuhara, Fujinomiya; Takeshi Shimomura, Fujinomiya; Naoto Uchida, Fujinomiya, all of Japan

[73] Assignee: Terumo Kabushiki Kaisha, Tokyo, Japan

[21] Appl. No.: 626,413

[22] Filed: Dec. 14, 1990

Related U.S. Application Data

[63] Continuation of Ser. No. 382,053, Jul. 13, 1989, abandoned, which is a continuation of Ser. No. 68,245, Jun. 30, 1987, abandoned.

[30] Foreign Application Priority Data

Jul. 1, 1986 [JP] Japan .................. 61-152744
Oct. 22, 1986 [JP] Japan .................. 61-249473
Apr. 3, 1987 [JP] Japan .................. 62-81276

[51] Int. Cl.⁵ .................. G06F 15/00; A61B 5/05
[52] U.S. Cl. .................. 364/413.11; 128/635
[58] Field of Search .................. 364/413.11, 413.03; 128/631, 635; 374/172

[56] References Cited

U.S. PATENT DOCUMENTS

| | | | |
|---|---|---|---|
| 3,781,092 | 12/1973 | Sussman et al. | 350/266 |
| 4,122,719 | 10/1978 | Carlson et al. | 374/172 X |
| 4,385,274 | 5/1983 | Shimida | 324/71.6 |
| 4,473,841 | 9/1984 | Murakoshi et al. | 128/6 X |
| 4,484,050 | 11/1989 | Horinouchi et al. | 374/172 X |
| 4,493,692 | 1/1985 | Reed | 128/635 |
| 4,538,617 | 9/1985 | Jensen | 128/635 |
| 4,618,929 | 10/1986 | Miller et al. | 364/413.11 |
| 4,690,147 | 9/1987 | Ooe et al. | 728/635 |
| 4,700,709 | 10/1987 | Kraig | 128/635 |
| 4,774,956 | 10/1988 | Kruse et al. | 364/413.11 X |
| 4,781,798 | 11/1988 | Gough | 128/635 |
| 4,792,980 | 12/1988 | Shimizu | 382/41 X |
| 4,844,623 | 7/1989 | Wada | 374/172 X |
| 4,847,794 | 7/1989 | Hrubes | 374/172 X |

FOREIGN PATENT DOCUMENTS

| | | |
|---|---|---|
| 21172 | 5/1984 | Australia . |
| 0171927 | 2/1986 | European Pat. Off. . |
| 55-129900 | 10/1980 | Japan . |
| 56-109645 | 8/1981 | Japan . |
| 61-288834 | 12/1986 | Japan . |
| WO81/01505 | 6/1981 | PCT Int'l Appl. . |
| 86/01919 | 3/1986 | PCT Int'l Appl. . |

Primary Examiner—Dale M. Shaw
Assistant Examiner—Xuong M. Chung
Attorney, Agent, or Firm—Burns, Doane, Swecker & Mathis

[57] ABSTRACT

A biological information measurement apparatus is adapted to measure biological information in an extracorporeal circuration or in a living body by various measurement circuits comprising circuit elements which are not affected by electrical disturbances, and to transmit the results of measurement in the form of a non-electrical signal which is not affected by electrical disturbances. Measured values from measurement sections are gathered at a central processing section separated from the measurement sections. The processing section converts the measured values into output values, compensates the values for temperature and outputs the values to a display unit and recorder.

9 Claims, 28 Drawing Sheets

BIOLOGICAL INFORMATION MEASUREMENT APPARATUS

This application is a continuation of application Ser. No. 382,053, filed Jul. 13, 1989, abandoned, which is a continuation of application Ser No. 068,245, filed Jun. 30, 1987, abandoned.

BACKGROUND OF THE INVENTION

1. Field of the Invention

This invention relates to an apparatus for measuring biological information. More particularly, the invention relates to a biological measurement apparatus used to sensing and monitoring a specimen in an extracorporeal circuration, or to perform sensing and monitoring in vivo.

2. Description of the Prior Art

In clinical and medical fields, the continuous measurement and monitoring of ion concentration, gas concentration and the concentration of biological substances, especially enzymes, is desirable. Though an appreciation of continuous monitoring is growing in general medical treatment, a practical continuous monitoring system has not yet been realized. There are various reasons for this. One is that ion sensors and sensors for identifying biological substances do not operate stably in a living body or in biological solutions. Another is that ion sensors, gas sensors and enzyme sensors, which typically are glass electrodes, generally have a high impedance which renders them susceptible to adverse electrical effects. As a result, satisfactory monitoring circuits are not available. Moreover, when monitoring is performed over an extended period of time, variations of temperature affect measurement precision, thus making it difficult to achieve highly precise monitoring. Furthermore, owing to the influence of electrical disturbances, there is a limit upon how far apart the measurement section and processing section of the system can be separated from each other.

SUMMARY OF THE INVENTION

An object of the present invention is to provide a biological information measurement apparatus for measuring such biological information as the concentration of a specimen in an extracorporeal circulation using biological living body fluids and biological solutions, and in a fluidic solution.

Another object of the present invention is to provide a biological information measurement apparatus in which measured values are temperature-compensated in response to temperature variations in living body fluids, biological solutions and measuring devices.

Still another object of the present invention is to provide a biological information measurement apparatus in which a measurement section and processing section are separated via transmission means not susceptible to the influence of electrical disturbances, whereby the measurement section can be made easy to handle and remote centralized supervision performed by the processing section can be facilitated.

A further object of the present invention is to provide a biological information measurement apparatus in which sensor output (current, electromotive force, resistance, etc.) can be measured stably and very accurately.

The present inventors have already proposed ion sensors, gas sensors and enzyme sensors suitable for continuous monitoring and have succeeded in fabricating the aforementioned biological information measurement apparatus as the result of exhaustive research relating to continuous measurement systems suitable for use in the medical field for stable, highly precise measurement of ion concentration, gas concentration and the like.

According to the present invention, the foregoing objects are attained by providing a biological information measurement apparatus comprising measuring means for measuring biological information continuously, transmitting means for non-electrically transmitting a biological information signal outputted by the measuring means, converting means for converting the biological information signal transmitted by the transmitting means into an electrical signal, analyzing means for analyzing the biological information signal, which has been converted into the electrical signal by the converting means, in dependence upon the type of biological information, and output means for outputting analytical results from the analyzing means to an external unit, the analytical results being made to correspond to the type of biological information.

In a preferred embodiment of the invention, the transmitting means comprises optical communication means having one or a plurality of optical fiber cables.

In a preferred embodiment of the invention, the output means comprises display means or memory means.

In a preferred embodiment of the invention, the measuring means includes an internal power supply.

In a preferred embodiment of the invention, the measuring means includes a differential amplifier as means for measuring electromotive force, the amplifier having an input resistance of at least $10^{11}\Omega$.

In a preferred embodiment of the invention, the measuring means includes temperature measuring means for measuring the temperature of a biological information measuring section in order to temperature-compensate the biological information measuring section.

In a preferred embodiment of the invention, the measuring means includes temperature measuring means for measuring the temperature of a living body in order to temperature-compensate the measured biological information.

Thus, the invention makes it possible to provide a biological information measurement apparatus for measuring such biological information as the concentration of a specimen in an extracorporeal circulation using biological living body fluids and biological solutions, and in a fluidic solution.

Further, it is possible to provide a biological information measurement apparatus in which measured values are temperature-compensated in response to temperature fluctuations in living body fluids, biological solutions and measuring devices.

Further, it is possible to provide a biological information measurement apparatus in which a measurement section and processing section are separated via transmission means not susceptible to the influence of electrical disturbances, whereby the measurement section can be made easy to handle and remote centralized supervision performed by the processing section can be facilitated.

Moreover, it is possible to provide a biological information measurement apparatus in which sensor output (current, electromotive force, resistance, etc.) can be measured stably and very accurately.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

A preferred embodiment of the present invention will now be described in detail in accordance with the accompanying drawings.

Figure 1:
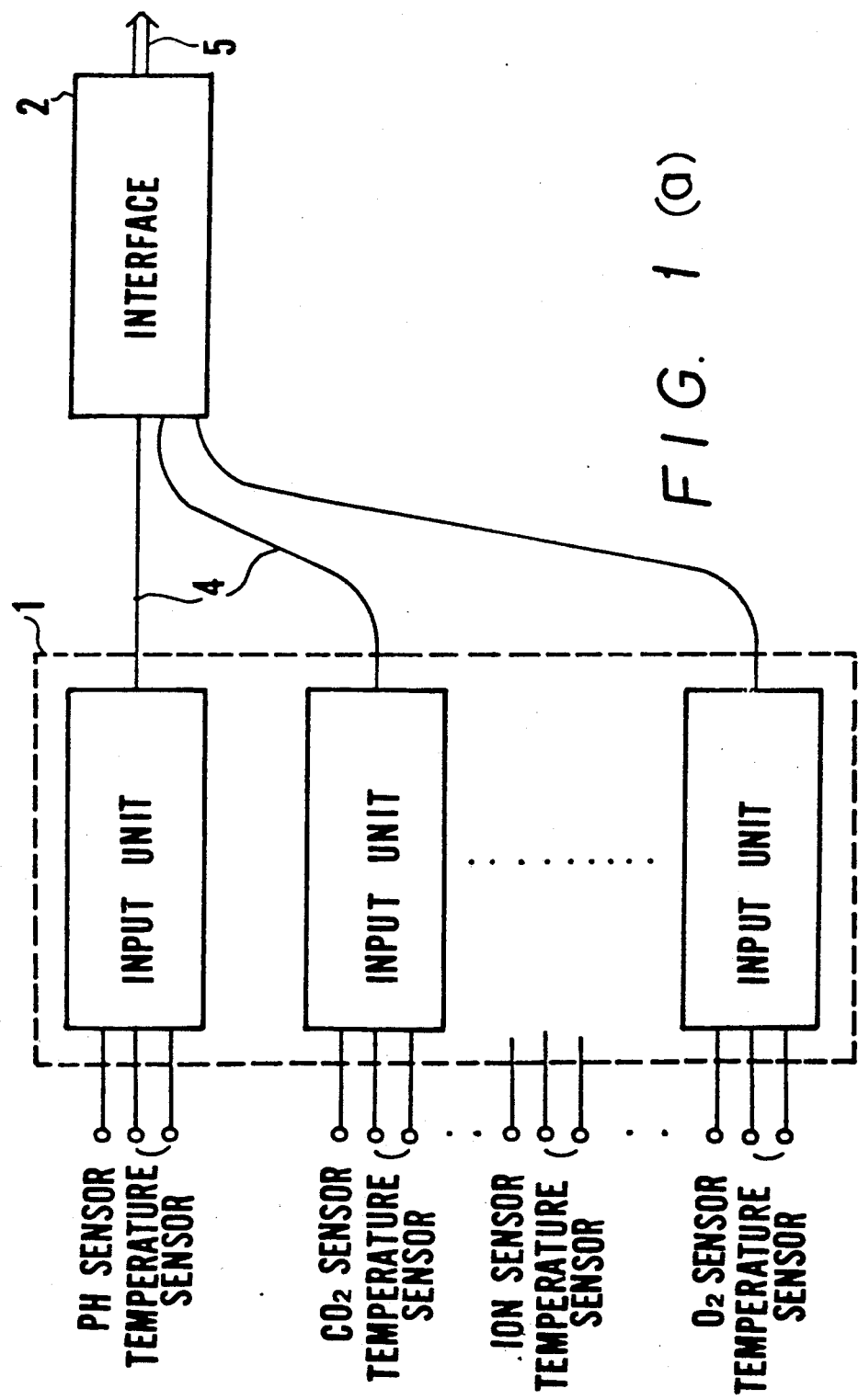
FIGS. 1(a), (b) are block diagrams illustrating an embodiment of a biological information measurement apparatus according to the invention.
Figure 1:
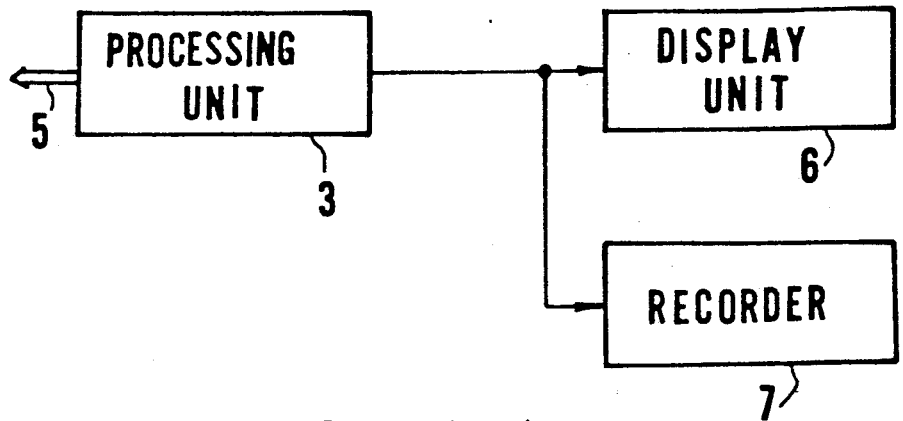

FIGS. 1(a), (b) are block diagrams illustrating an embodiment of a biological information measurement apparatus according to the invention. The apparatus comprises an input unit 1, an interface 2 and a processing unit 3. The input unit 1 and interface 2 are interconnected by optical fiber cables 4, and the interface 2 and processing unit 3 are connected by an electrical cable 5. The results of processing executed by the processing unit 3 are outputted to a display unit 6 and recorder 7.

Conventionally, the input unit 1 and interface 2 are integrated and an output section for the measurement data is isolated by a photocoupler or the like. If the input unit 1 has a high input-impedance, however, further isolation is required. In the illustrated embodiment, the input unit 1 is reduced in size, a primary or secondary battery is used and the output signal is converted into a optical signal which is then transmitted by the optical fiber cables 4. This assures a high degree of isolation. As a result, the superposition of noise entering through ground circuitry and the power supply can be reduced to make highly precise measurement possible. This also facilitates remote measurement and monitoring.

The input unit 1 measures one or more sensor outputs, such as electromotive force, current and resistance value. After the measured value, which is an analog quantity, is converted into a digital value, the resulting digital value is converted into an optical signal transmitted, through the optical cables 4, to the interface in the form of measurement data. If only one optical cable is used for transmitting the data, the outputs from a plurality of sensors can be transferred by a time-sharing method. A plurality of optical cables can be used if desired.

In an embodiment of the input unit 1, the input unit comprises a high-input resistance voltmeter for measuring the electromotive force of an ion sensor, and a circuit for measuring the output (resistance) of a temperature sensor for internally compensating the ion sensor and of a temperature sensor for measuring temperature in a solution.

FIGS. 2(a)-(d) are more detailed block diagrams showing the biological information measurement apparatus of the illustrated embodiment.

An input unit 1a is for measuring ion, gas and enzyme concentration and is adapted to simultaneously perform a temperature measurement for internal temperature compensation. To this end, the input unit 1a comprises a high-input resistance voltmeter 10 for measuring emf, thermometers 11, 12 for internal temperature measurement and solution temperature measurement, respectively, AD converters 13, 14, 15 for converting the outputs of the voltmeter 10 and thermometers 11, 12 into digital values, a multiplexer 16 for selecting the digital values resulting from the conversion, and an optical transmission circuit 17 for converting the digital values into optical signals and transmitting the optical signals to the interface 2.

Figure 3:
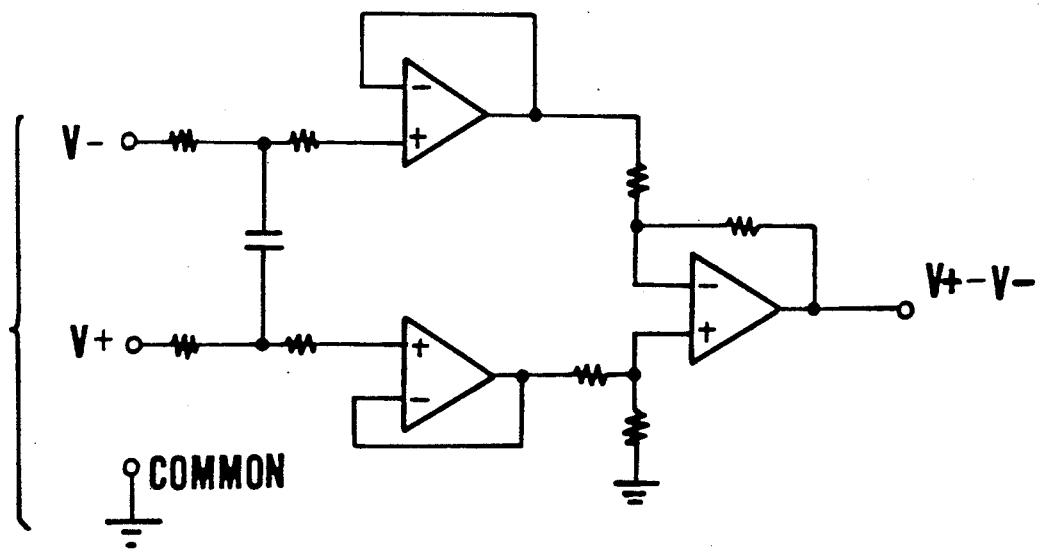
FIG. 3 is circuit diagram of a high-input resistance differential amplifier for an ion sensor.
Figure 2A:
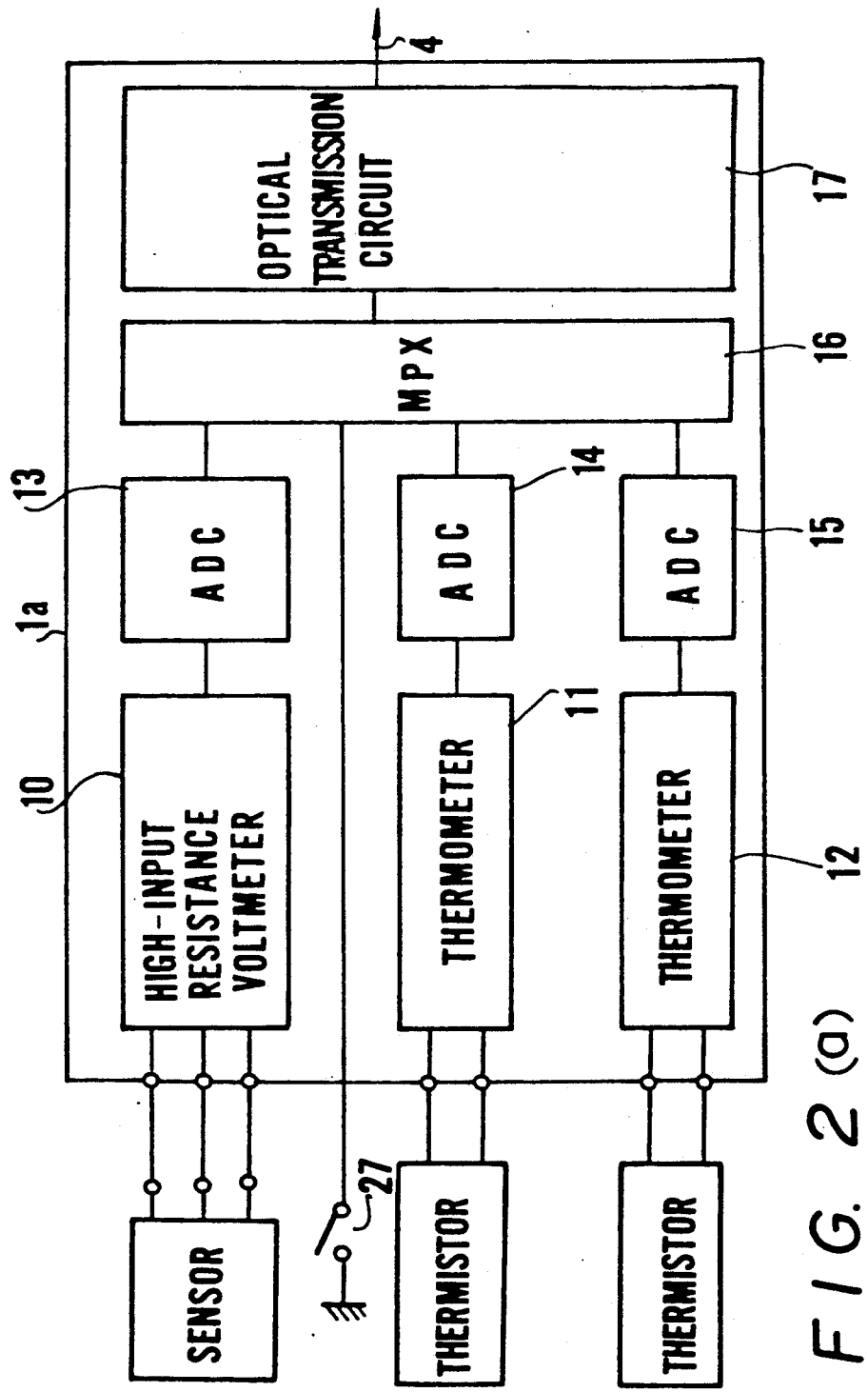
FIGS. 2(a)-(d) are more detailed block diagrams illustrating the embodiment of the biological information measurement apparatus according to the invention.
Figure 2B:
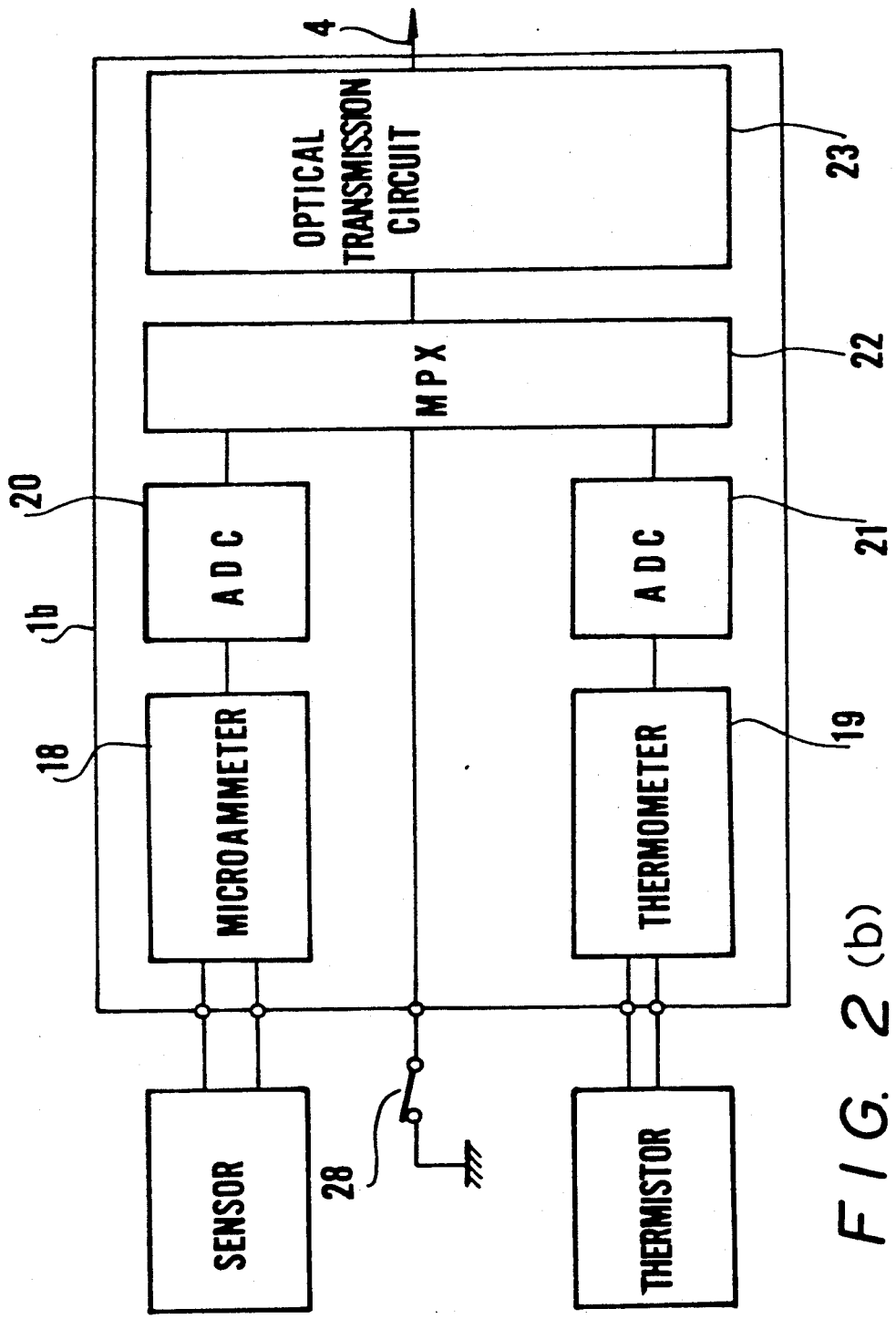
Figure 2:
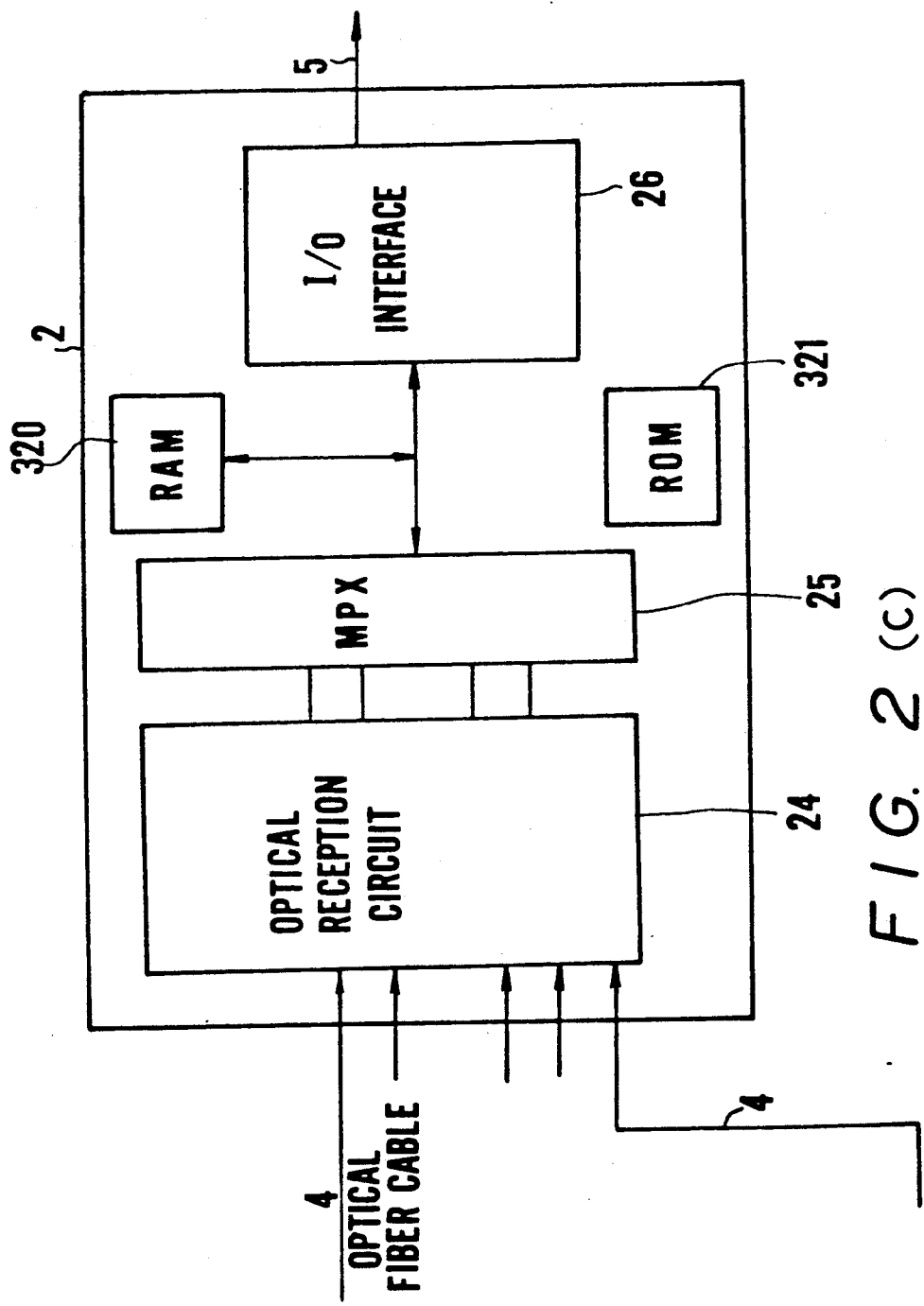
Figure 2:
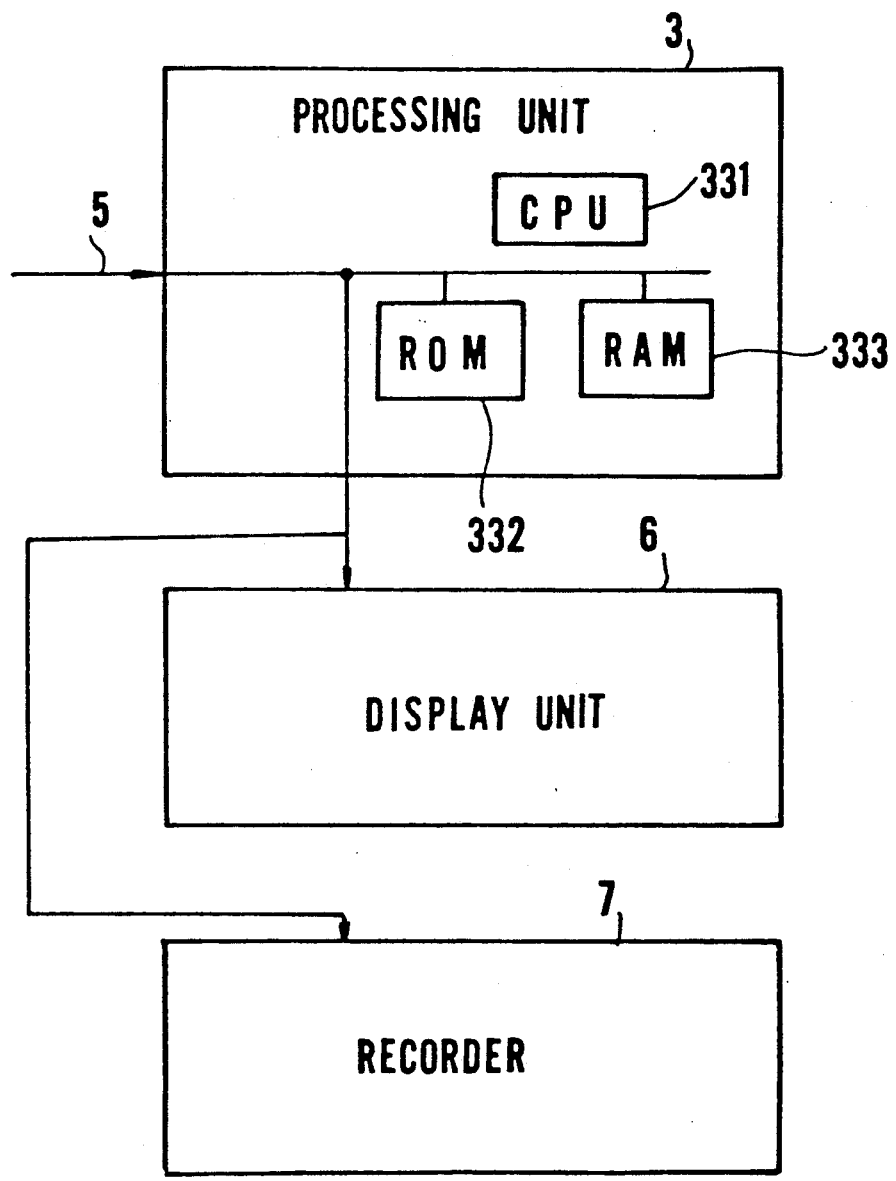

FIG. 3 illustrates an example of a high-input resistance differential amplifier for an ion sensor, which amplifier is used as a high-input resistance voltmeter for measuring emf. The high-input resistance voltmeter 10 comploys a high-input impedance (no less than $10^{11}\Omega$), low-drift (less than $2\ \mu V/C^0$) differential amplifier constituted by a readily available operational amplifier (e.g. the OPA111BM, manufactured by Burr-Brown Co. or the TLC-27L2 manufactured by Texas Instruments). The AD converters 13, 14, 15 are double integrating-type, $4\frac{1}{2}$-digit AD converters (the ICL7135CPI, manufactured by Intersil Inc.). The multiplexer 16 and digital circuitry are constituted by a CMOS logic IC in order to reduce power consumption. The AD converters 13, 14, 15 are started simultaneously e.g. every 400 ms and perform a serial conversion, with header characters being assigned to their respective output values.

Figure 4:
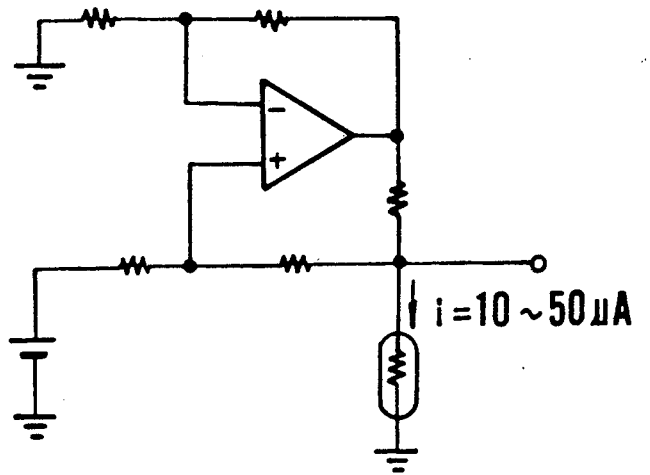
FIG. 4 is a circuit diagram of a circuit for measuring temperature.

FIG. 4 shows and examples of a temperature measuring circuit. The thermometers 11 and 12 each include a readily available operational amplifier to construct a highly accurate constant-current source. Preferably, the constant-current source is set to no more than 70 μA, with a current range of 10 μA–50 μA being especially preferred. A circuit in which the amount of power consumed by a temperature sensor element (thermister) is less than 50 μW may be provided as the constant-current source. Preferably, the circuit should be designed so that the amount of power consumed by a temperature sensor element (thermister) is 20 μW. The voltage that results when this constant current flows through the temperature sensor element (thermister) is measured by the analog to digital (AD) converter 14, or 15. During calibration of the apparatus, a signal indicative of the fact is generated by a switch 27. This signal is delivered to the interface 2 by the multiplexer 16.

In order for the biological information measurement apparatus of the embodiment to measure biological information continuously with a high accuracy, it is required that temperature measurement and temperature compensation based on this measurement be performed quickly and accurately. In particular, it is required that temperature be measured with an accuracy of within 0.01° C. Accordingly, in order to measure temperature in the illustrated embodiment, a thermister is used and not a thermocouple or platinum resistor requiring a high-performance device. Further, in view of the fact that the thermister is inserted into a living body, use is made of a miniature thermister inserted into an insulative tube. In order to reduce an error due to self-heating, the value of the constant current that flows through the thermister is set to 50 μA in the illustrated embodiment.

In a conventional thermister thermometer of simple type, the thermometer includes a linearizing circuit obtained by connecting a fixed resistor in series with the thermister element. Since temperature is measured with such an arrangement, accuracy is limited to ±0.5 C°. This can be understood from the following equation for calculating temperature T (°K) from the resistance value R (ohm) of a thermister:

$$1/T - 1/T_0 = 1/B \ln(R/R_0)$$

where $R_0$ (ohm) represents the resistance value at the temperature $T_0$(°K). Further, B is a function of temperature, though this can be regarded as a constant in a narrow temperature range (e.g. ±2° C.). For this reason, highly precise measurements cannot be taken with the aforementioned linearizing circuit in a broad temperature range (e.g. 0–50° C.). By using the temperature $T_0$, B is expressed as follows in a range $T_1$ (°K):

$$B = B_0 + C(X - X_0) + E \cdot T_0(T - T_1) + F \cdot T_0(T - T_1)(T + T_0 + T_1)$$

where $X = \ln(T/T_0)/1/(T_0 - 1/T)$
In the above, $B_0$, C, $X_0$, E and F are constants and represent physical values related to the composition of the thermister.

In the illustrated embodiment, the resistance values from the thermisters are converted into digital values by the AD converters 14, 15 and an AD converter 21 and the digital values are transmitted to the processing unit 3 via the optical fiber cables 4, interface 2 and cable 5. On the basis of these values, the processing unit 3 calculates temperature rapidly and accurately in accordance with an arithmetic program, described below.

Figure 5:
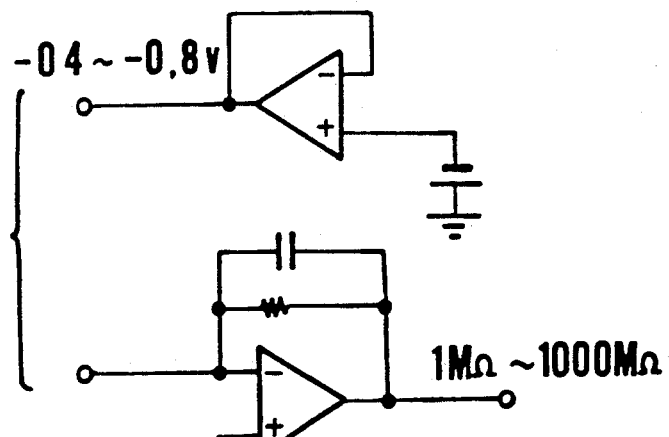
FIG. 5 is a circuit diagram of a polarographic microcurrent measuring circuit.

The input unit 1b is adapted to measure the concentration of $O_2$ by measuring the polarographic current of $O_2$, by way of example, and includes a microammeter 18, a thermometer 19 for temperature measurement, AD converters 20, 21, a multiplexer 22 and an optical transmission circuit 23. The microammeter 18 comprises a $-0.5$ V $\sim -0.7$ V constant-voltage source, and a circuit for converting a microcurrent of $10^{-6} \sim 10^{-11}$A into a voltage. FIG. 5 illustrates an example of a polarographic microcurrent measuring circuit.

The AD converters 20, 21 are double integrating-type, 4½-digit AD converters (the ICL7135CPI, manufactured by Intersil Inc.). The multiplexer 22 and digital circuitry are constituted by a CMOS logic IC in order to reduce power consumption. The AD converters 20, 21 are started simultaneously e.g. every 400 ms and perform a serial conversion, with header characters being assigned to their respective output values.

The thermometer 19 includes a readily available operational amplifier to construct a highly accurate constant-current source. Preferably, the constant-current source is set to no more than 70 μA, with a current range of 10 μA–50 μA being especially preferred. The voltage that results when this constant current flows through the temperature sensor element (thermister) is measured by the AD converter 21. During calibration of the apparatus, a signal indicative of the fact is generated by a switch 28. This signal is delivered to the interface 2 by the multiplexer 22.

The interface 2 includes an optical reception circuit 24 having a plurality (e.g. five in the illustrated embodiment) of input channels for converting optical signals from the input unit 1 into electric signals, a multiplexer 25 for selecting a channel of signal data, and an Input/Output (I/0) interface 26 for transmitting the signal data selected by the multiplexer 25 to the processor 3. The latter converts the signal data into concentration units before outputting the data to the display unit 6 and recorder 7.

The signal data are not only outputted to the memory unit 6 and recorder 7 but are also stored in a memory device so that they may be read out whenever required. Though the measurement data received from the input unit 1 may be delivered directly to the processing unit 3, the burden on the processing unit 3 can be reduced if the interface 2 is provided with a Random Access Memory (RAM) 320 and the measurement data are arranged and temporarily stored in the RAM 320 in accordance with a program stored in a ROM 321. The multiplexer 25 uses an eight-bit Central Processing Unit (CPU) to convert the received data into character and numerical value codes, stores these channel by channel and transfers the data in response to a data request from the I/0 interface 26. The I/0 interface 26 uses an IEEE-488 bus interface, but a general-purpose RS-232C or the like can also be used.

The central processing unit 3 comprises a CPU 331, a ROM 332 for storing a processing program, and an auxiliary RAM 333 and converts the signal from the interface 2 into units of ion concentration or gas partial pressure (concentration) by performing a calculation in accordance with a calibration curve prepared in advance. The processing unit 3 is also capable of compensating for a temperature fluctuation in a sensor by using sensor temperature. A personal computer having an eight-bit CPU or 16-bit CPU can be utilized as the processing unit 3. By assembling the interface 2 on a board, the interface can be inserted into the expansion slot of a personal computer.

Figure 6C:
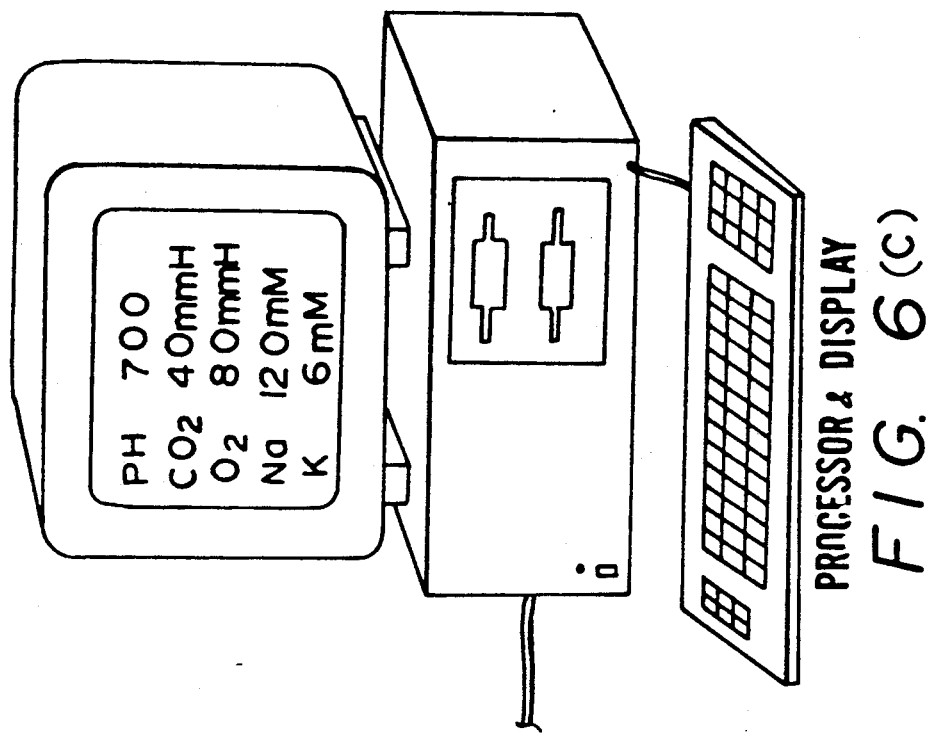
FIG. 6(a)-(c) are views showing the general features of the embodiment of the biological information measurement apparatus.
Figure 6A:
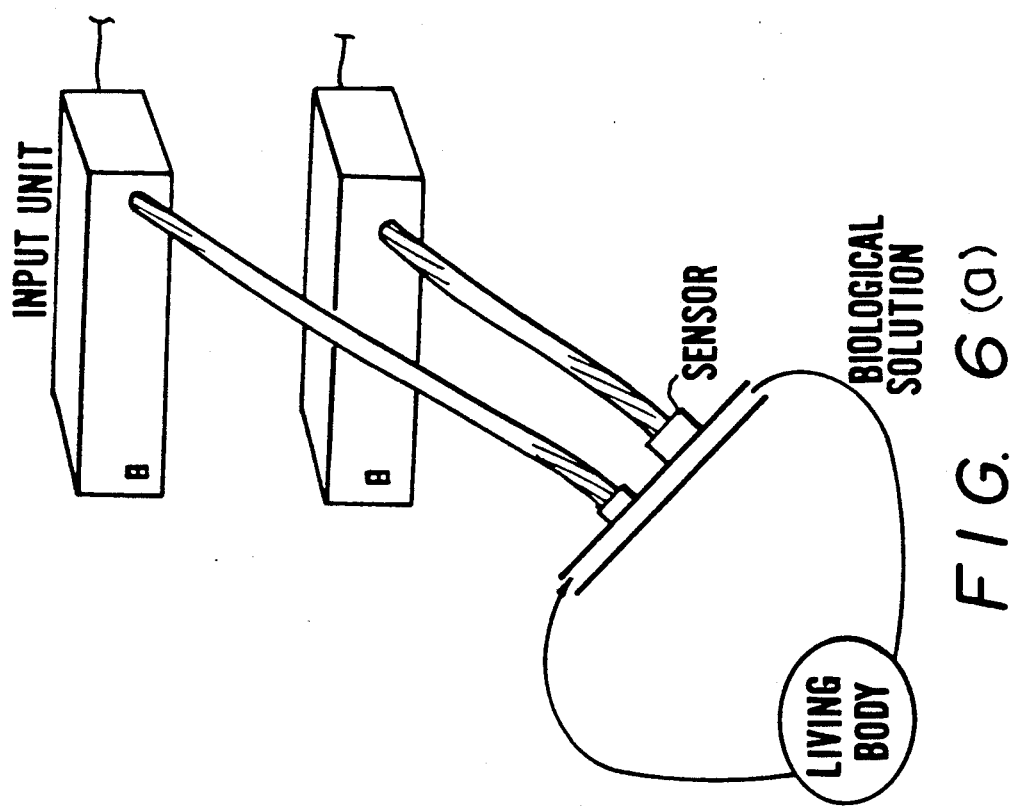
Figure 6B:
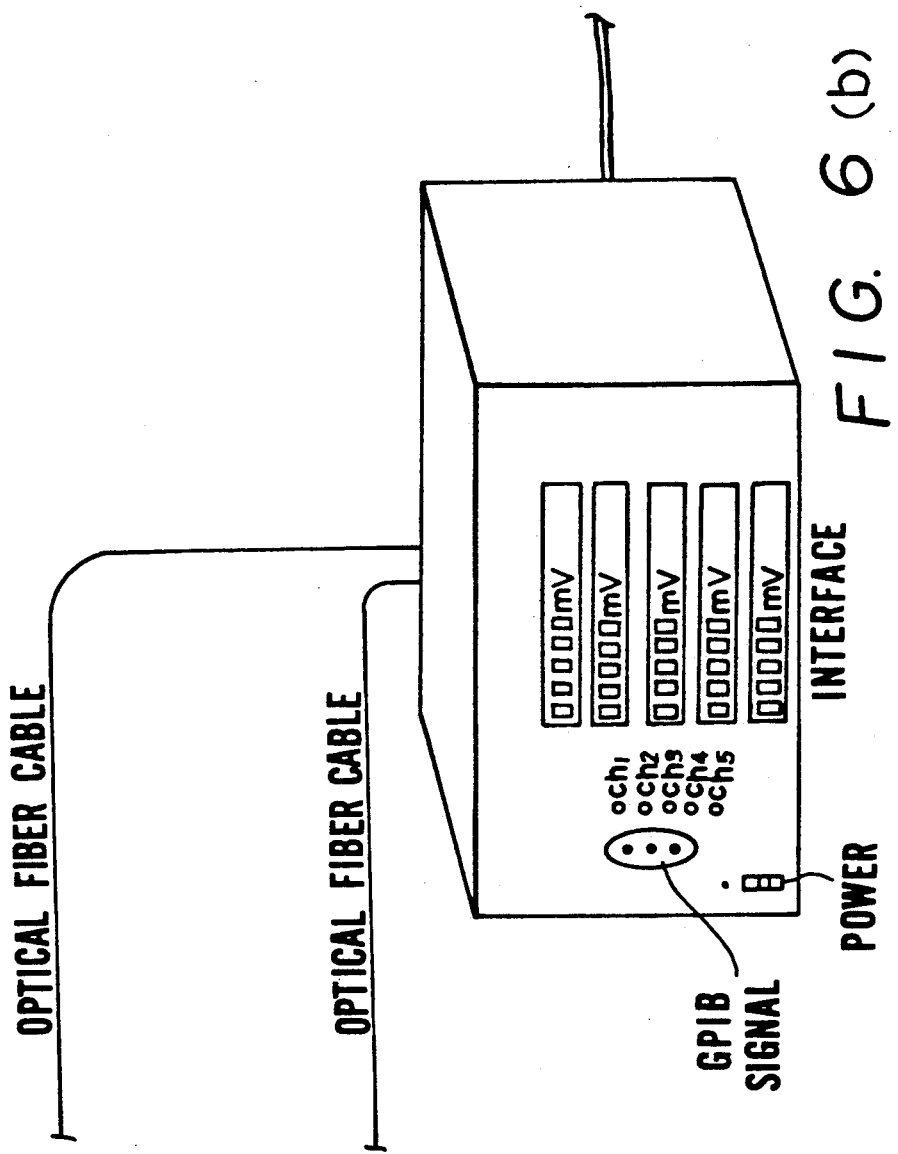
Figure 7:
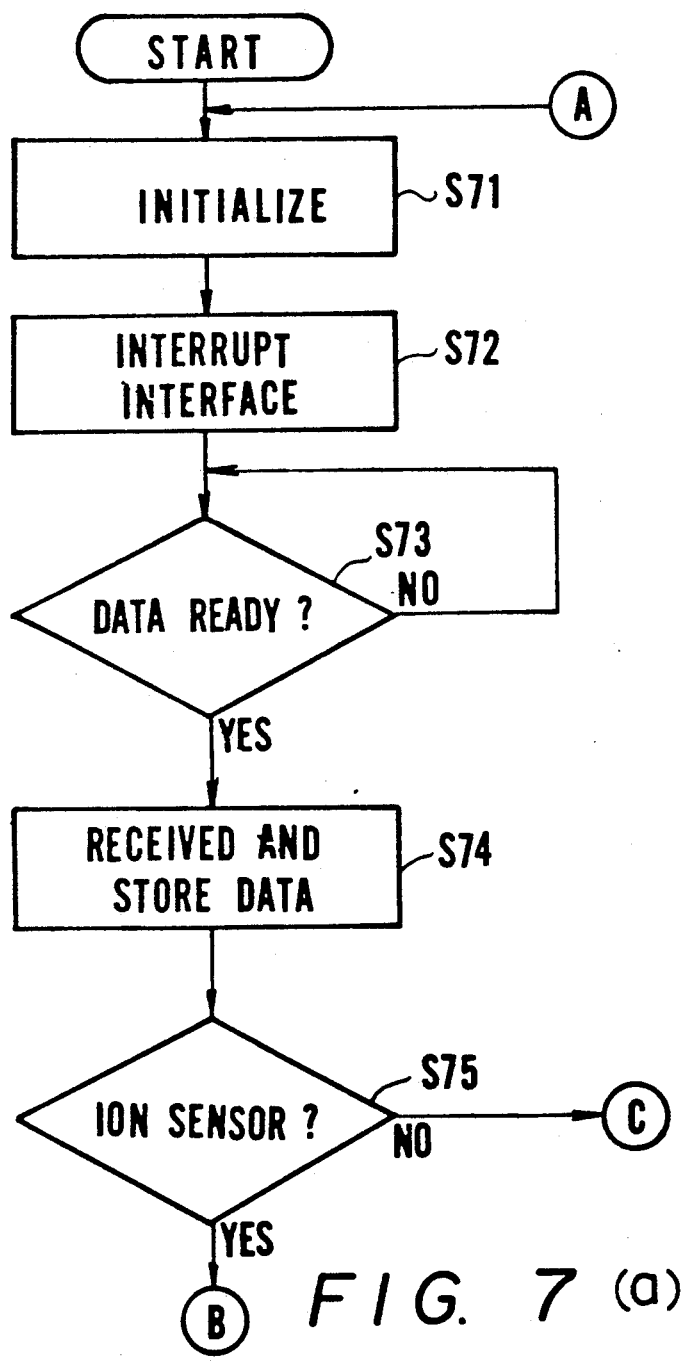
FIGS. 7(a)-(e) are flow charts of a control program executed by a processing unit.
Figure 7B:
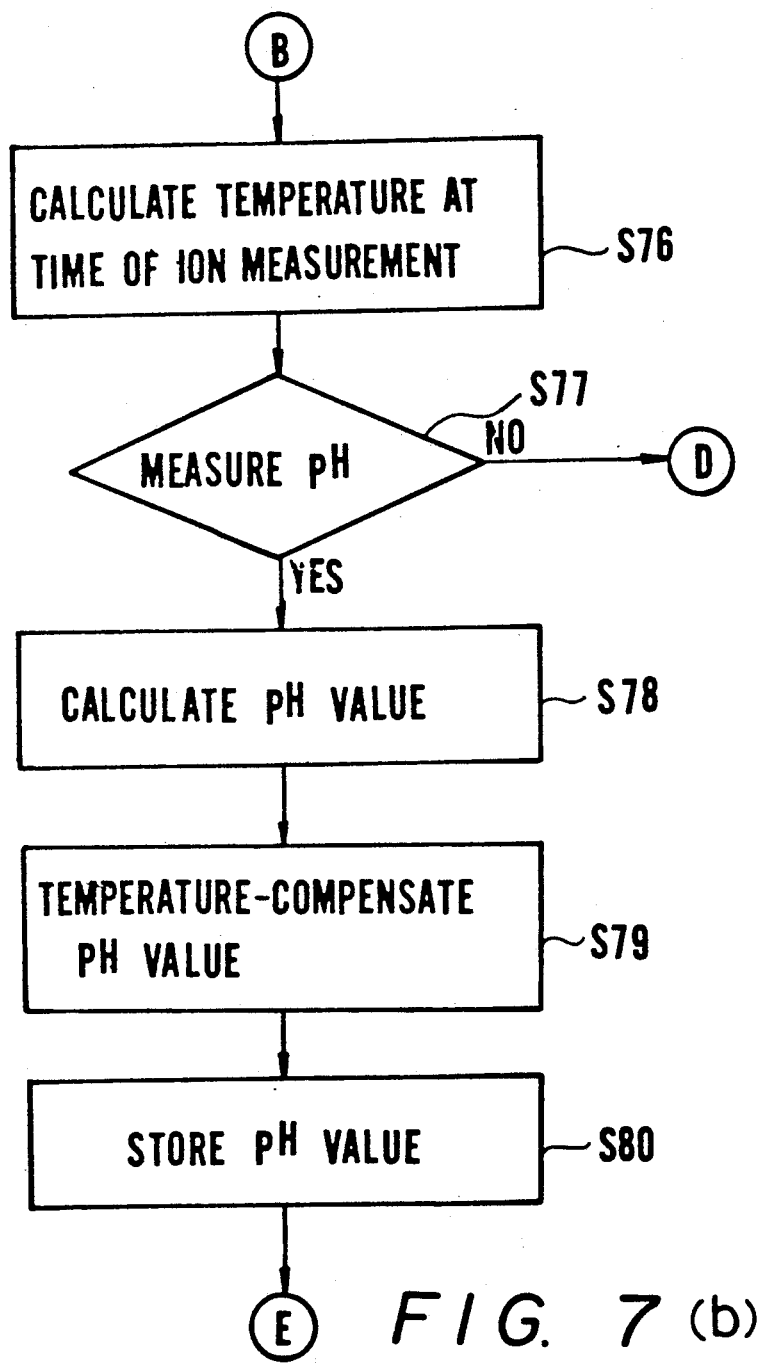
Figures 7C, 8A:
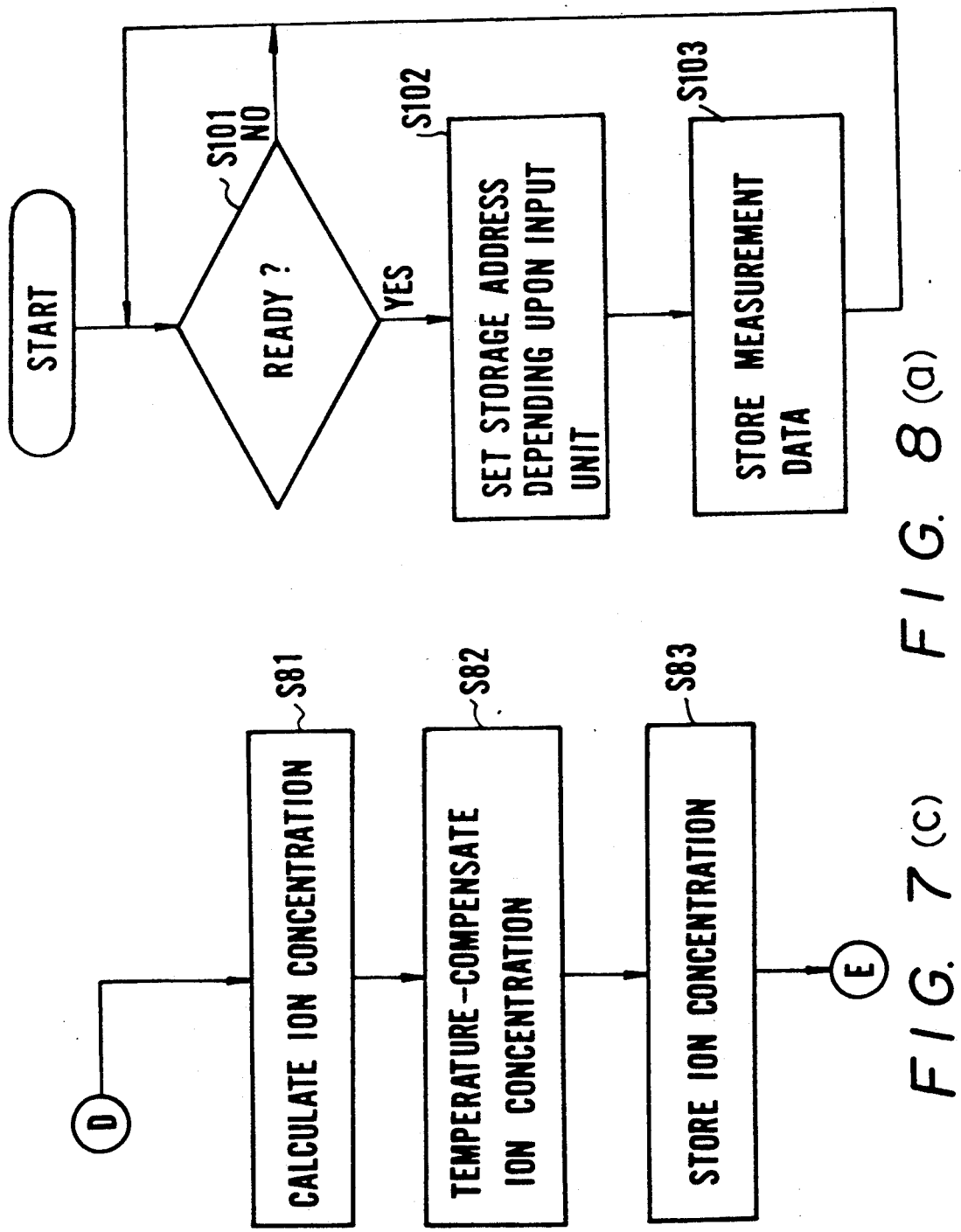
FIGS. 8(a), (b) are flow charts illustrating a control program of an interface.
Figure 7:
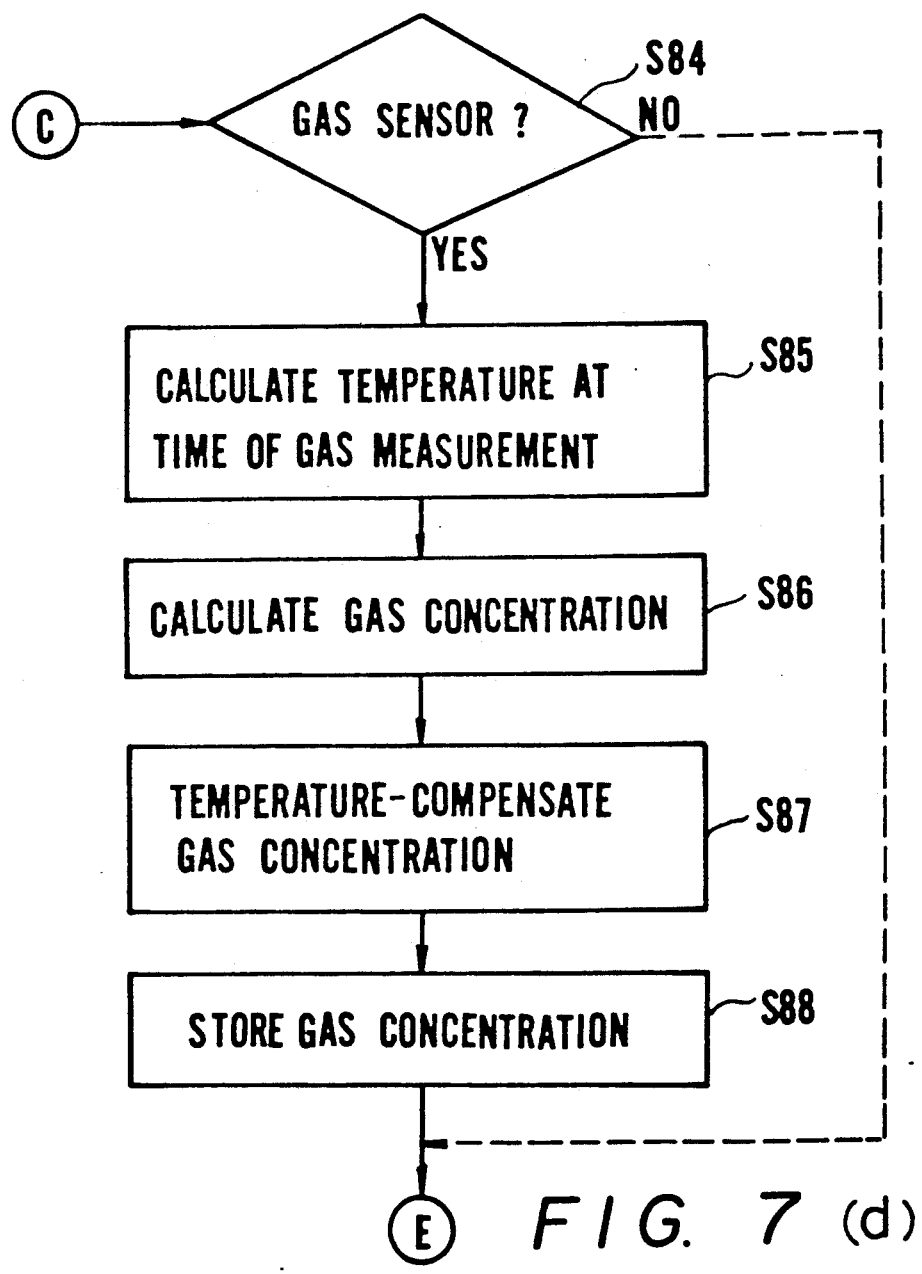
Figure 7:
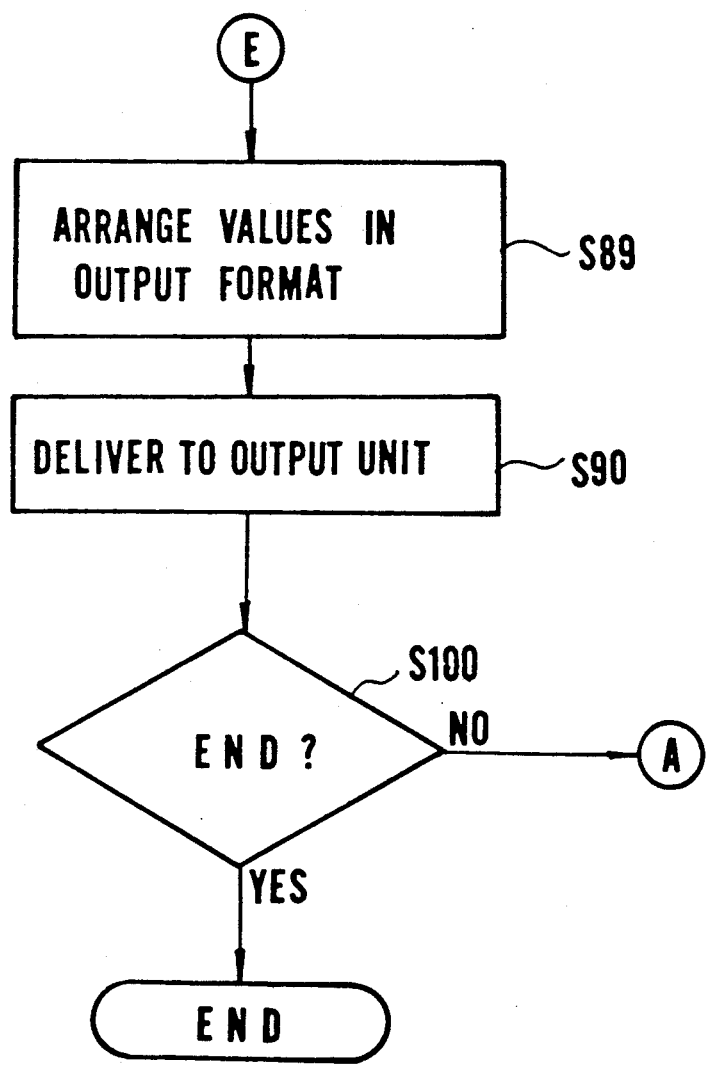

FIGS. 6(a)–(c) are views showing the general features of the embodiment of the biological information measurement apparatus, FIGS. 7(a)–(e) are flow charts of a control program executed by the processing unit 3 and stored in the ROM 332, and FIGS. 8(a), (b) are flow charts illustrating the control program of the interface 2. This control program is stored in the ROM 321.

In FIGS. 7(a)–(e), the system is initialized at a step S71. Next, at a step S72, an interrupt demanding transmission of the measurement data is applied to the interface 2. The program then proceeds to a step S73, where the system waits for the measurement data to arrive from the interface 2.

Meanwhile, the interface 2 receives the measurement data from the input unit 1 while scanning these data in accordance with the procedure of FIG. 8(a). Specifically, at a step S101, the interface 2 waits for the arrival of the measurement data from the input unit 1. Then, at a step S102, a different storage address is set depending upon the connection position of the input unit 1. This is followed by a step S103, at which measurement data are stored in a storage area of RAM 320 that depends upon the input unit 1. Execution of the steps S101 through S103 is repeated to store the measurement data while all of the input units 1 are scanned in order. Though storage addresses which differ depending upon the connection positions are set to distinguish the differences in biological data measured, it is also permissible to adopt an arrangement in which measurement data from the input units 1 are provided with identification codes for identifying the type of biological data. This will have the advantage of raising the degree of freedom of control since the types of biological information can be identified without taking the connection positions into consideration.

Figure 8B:
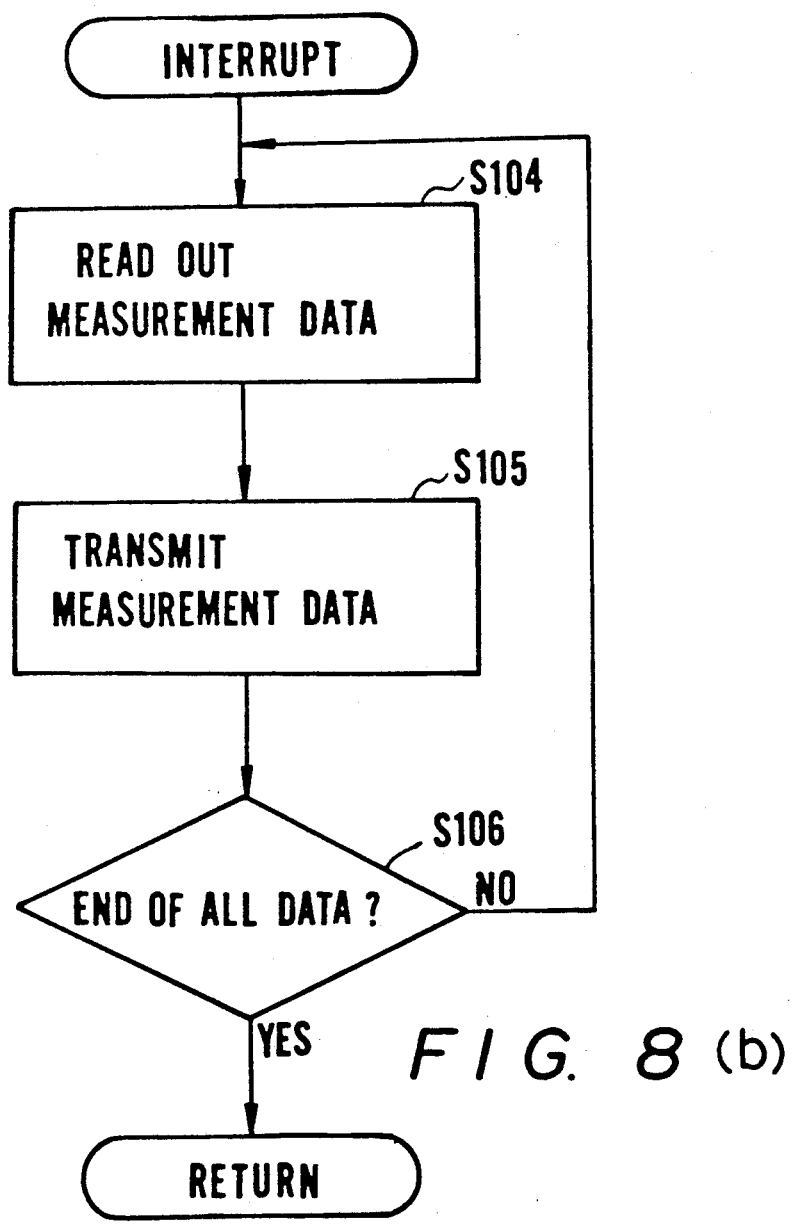

If there is an interrupt from the processing unit 3 calling for the transmission of measurement data, processing is executed through the procedure shown in FIG. 8(b). First, the measurement data stored at the step S103 of the ordinary procedure [FIG. 8(a)] are read out at a step S104, and the data are transmitted to the processing unit 3 at a step S105. Next, it is determined at a step S106 whether the transmission of all measurement data has ended. If the answer at this step is NO, then the program returns to the step S104 and steps S104 through S106 are repeated.

At a step S74 in FIGS. 7(a)–(e), the processing unit 3 receives the measurement data transmitted through the steps S104 through S106 and stores the data in the RAM 333. Next, analysis that differs depending on the type of stored measurement data is performed at steps S75 and S84. The invention will be described for a typical case in which the system includes an ion sensor and gas sensor. Processing would be performed through a similar procedure for biological information from other sensors as well.

In the case of the ion sensor, the program proceeds from the step S75 to a step S76, where the temperature which prevails at the time of ion measurement is calculated from temperature measurement data obtained from the input unit corresponding to the ion sensor. A step S77 calls for a determination as to whether pH is to be measured. If the answer is YES, then the pH value is calculated from the measurement data at a step S78, the pH value is corrected at a step S79 based on the temperature calculated at the step S76, and the corrected pH value is stored at a step S80. If the decision rendered at the step S77 is that pH is not to be measured, then the concentration of another ion is calculated, compensated for temperature and stored through steps S81 through S83.

In the case of the gas sensor, the program proceeds from the step S84 to a step S85, where the temperature which prevails at the time of measurement performed by the gas sensor is calculated from temperature measurement data obtained from the input unit corresponding to the gas sensor. Gas concentration is calculated, compensated for temperature and stored at steps S86 through S88.

A step S89 calls for the stored results of the various measurements to be arranged in accordance with the output formats of the display unit 6 and recorder 7. These results are outputted to the display unit 6 and recorder 7 at a step S90. Next, it is determined at a step S100 whether measurement has ended. If the answer is NO, the steps S71 through S100 are repeated to output the results of measurement obtained next. It should be noted that multifarious control is possible, such as outputting predetermined biological information if it exceeds an allowable value, even if the results of measurement are outputted at a fixed timing.

Figure 9:
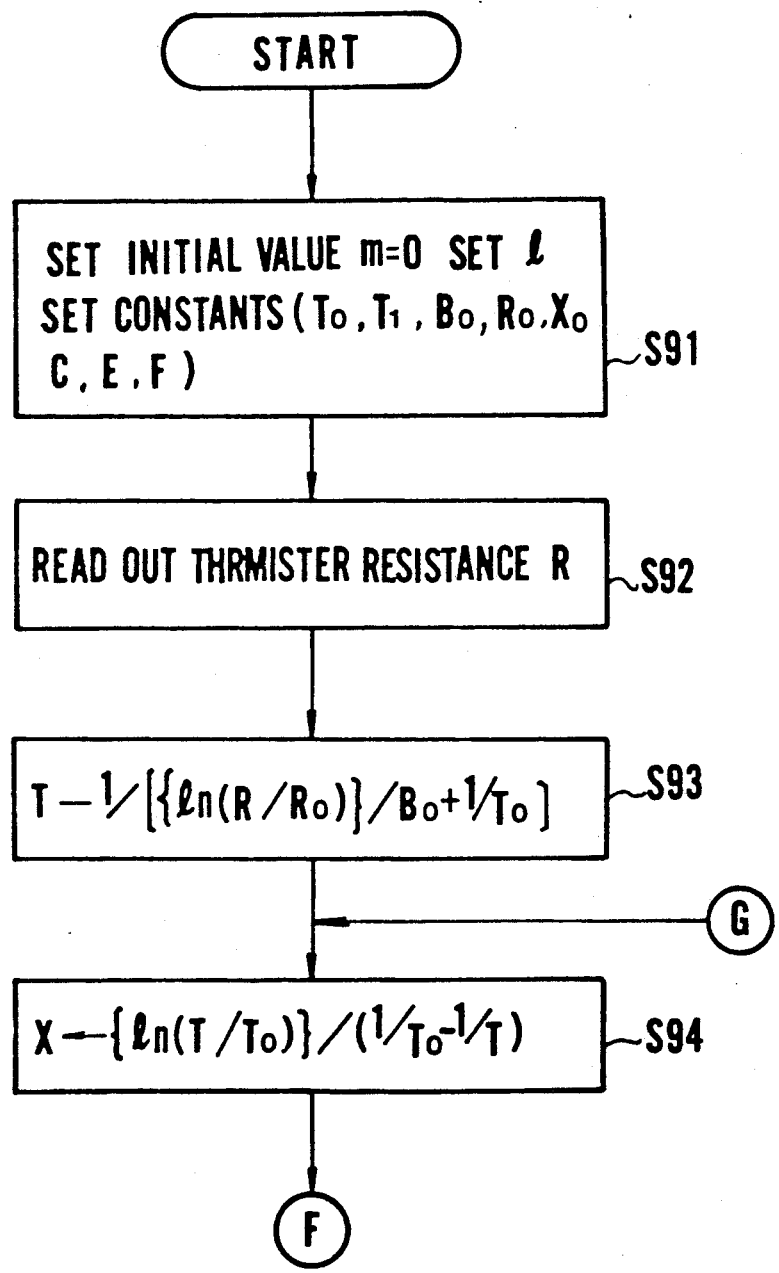
FIGS. 9(a), (b) are flow charts of a program for measured temperature calculation.
Figure 9:
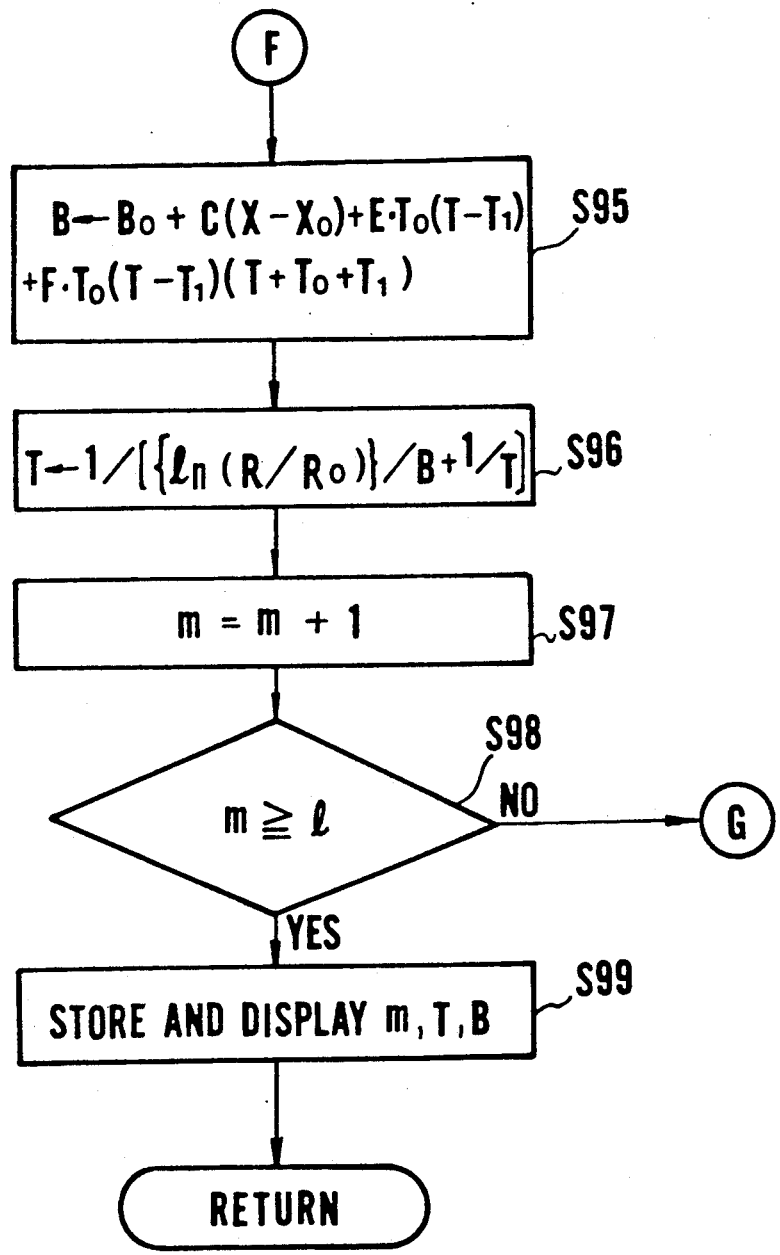

FIGS. 9(a), (b) illustrate flow charts for the calculation of measured temperatures (also known as the convergency technique) performed at the steps S76, S85. In FIGS. 9(a), (b), m represents the value of a count recorded by a counter, and l represents the number of times a calculation is repeated for reasons of accuracy.

At a step S91, m is set to 0 as an initial value, l is set to a predetermined number, and constants $T_0$, $T_1$, $B_0$, $R_0$, $X_0$ C, E and F are set. Next, at a step S92, the stored thermister resistance value R received from the interface 2 together with the other measured values at the step S74 is read. This is followed by a step S93, at which T is calculated on the basis of R using the following equation:

$$T = 1/[\{(ln(R/R_0)\}/B_0 + 1/T_0]$$

Next, X is calculated on the basis of T, obtained at the step S93, in accordance with the following equation:

$$X = [ln(T/T_0)/(1/T_0 - 1/T)$$

Then, on the basis of T calculated at the step S93 and X calculated at the step S94, B is calculated from the following equation at a step S95:

$$B = B_0 + C(X - X_0) + E \cdot T_0(T - T_1) \\ + F \cdot T_0(T - T_1)(T + T_0 + T_1)$$

The program then proceeds to a step S96, at which T is calculated anew based on T calculated at the step S93 and B calculated at the step S95. Next, m is incremented at a step S97, and it is checked at a step S98 whether m is equal to or greater than the initially set l. If the answer is no, the program returns to the step S94 and steps S94 through S98 are repeated. If m is found to be equal to or greater than l at the step S98, the program proceeds to a step S99, at which the present values of m, T and B are stored, after which the program returns. It should be noted that l may be a fixed number or may be set to a number which will cause computation to be repeated until a change due to a single calculation of the value of T falls below a predetermined value.

EXPERIMENT 1

The thermister employed should be a miniature thermister inserted into a polyimide tube and having an outer diameter of no more than 1.00 mm. Preberable characteristics are $B_0 = 3244 \sim 3408$, $R_0 = 7400 \sim 7800$, $C = 30.7$, $E = -0.0766$, $F = 0.338 \times 10^{-4}$, with the thermal time constant being no more than 50 msec. In the present experiment, the thermister used had an outer diameter of 0.55 mm and the characteristics $B_0 = 3350$, $R_0 = 7793$, $C = 30.7$, $E = -0.0766$, $F = 0.338 \times 10^{-4}$, thermal time constant = 50 msec. Preferably, the constant current value is set to less than 70 $\mu$A to reduce the error ascribable to self-heating of the thermister, or a constant-current source is used that will hold the amount of power consumed by the thermister element to less than 20 $\mu$W. In the experiment, the circuit shown in FIG. 4 was employed so that the value of the constant current flowing through the thermister element would be 50 $\mu$A. Temperature was measured using a thermoregulator (CTE-24WS, Yamato Scientific Co. Ltd.) as a constant-temperature bath, and a temperature measuring device (D632, manufactured by Takara Thermistor Instruments Co. Ltd.) having an accuracy of 1/100° C. was used for comparison purposes. The results are shown in Table 1.

TABLE 1

| Number of calculation loops | This Invention (°C.) | D632 |
|---|---|---|
| n = 0 | 23.7935 | |
| n = 1 | 24.0817 | 24.082° C. |
| n = 2 | 24.0781 | |
| n = 3 | 24.0781 | |
| n = 4 | 24.0781 | |

It was found that an accuracy of 1/100° C. could be obtained by the first calculation loop. A difference of 0.002° C. from the value measured with the D632 for comparison purposes was obtained, indicating good agreement. This means that it is possible to measure temperature both rapidly and very precisely (measurement time: less than 100 msec). Similar results were obtained even using a constant-current source in which the amount of power consumed by the thermister element was less than 20 $\mu$W.

EXAMPLE 2

Temperature-compensated ion concentration measurement was performed by simultaneously measuring ion concentration and temperature using the apparatus shown in FIGS. 1(a), (b) and FIGS. 2(a)–(d).

The input unit 1a comprises the high-input resistance voltmeter 10 for ion concentration measurement, and the temperature measuring circuits 11, 12, identical with those used in Experiment 1. The outputs of the voltmeter 10 and circuits 11, 12 are converted into digital signals delivered to the multiplexer 16 and then transmitted as light signals by the optical transmitting circuit 17. The light signals are sent to the interface 2 on a time-sharing basis via the optical fiber cable 4. The interface 2 inputs the data to the processing unit 3. In the experiment, a GP-IB interface (IEEE-488) was used as the interface 2. A personal computer (PC-9801VM4, manufactured by Nippon Electric Co.) was used as the processing unit 3.

With an ion-selective electrode, ion concentration [ION] and electromotive force E are related by a Nernst equation. Specifically, in the case of an anion, the equation is expressed as follows:

$$E = E^0 + RT/nF \ln [ion] \quad [Ion] = exp[(nF/RT)(E-E^0)]$$

Therefore, if the temperature T and electromotive force E can be measured, then it is possible to perform a highly precise measurement of ion concentration without the influence of a change in temperature.

The continuous measurement of hydrogen ion concentration will now be described as a specific example.

The potential difference E of a pH sensor in each of three types of buffer solutions having a known temperature and pH was measured, the coefficients $a_1$, $b_1$, $c_1$ of the calibration equation $$E = a_1 T + b_1 T \text{ pH} + c_1 \quad (1)$$

Figure 10:
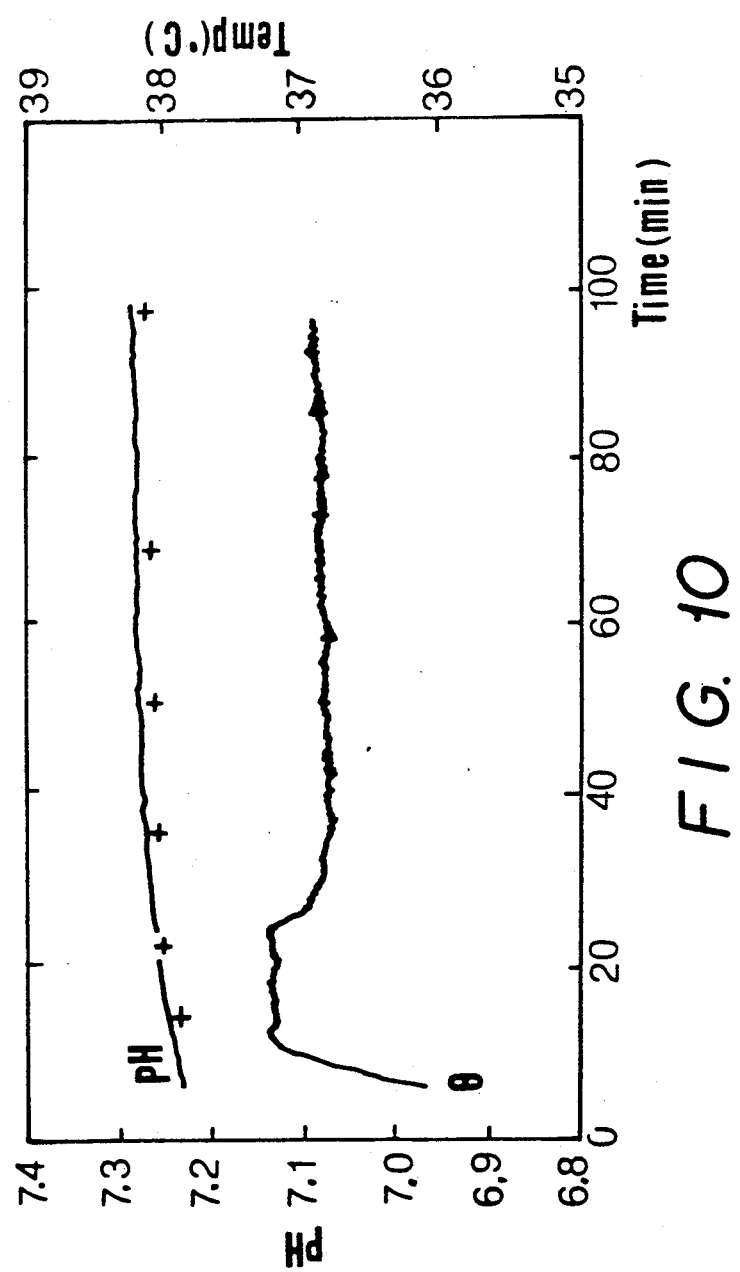
FIG. 10 is graph illustrating the results of measurement comprising temperature values and temperature-compensated pH values obtained with the biological information measurement apparatus of the embodiment.

(where T represents absolute temperature) were calculated, and a calibration equation was formed. Next, the pH sensor and a thermistor were set in a circulating standard blood serum (Precinorm® U, Boehringer Mannheim GmbH). The potential E of the pH sensor and the temperature T (= $\theta$ + 273.15) of the thermistor were read in by processing unit 3 through the input unit 1a, multiplexer 16, optical fiber 4 and interface 2, and the pH value of the circulating solution was calculated from Eq. (1). As shown in FIG. 10, the results indicate that the pH value can be measured very accurately even if the circulating solution temperature $\theta$ varies. In FIG. 10, the "+" marks indicate the values measured using a readily available pH sensor (the ABL3, manufactured by Radiometer Copenhagen).

EXPERIMENT 3

Temperature-compensated measurement of the partial pressure of carbon dioxide was performed by simultaneously measuring the partial pressure of carbon dioxide and temperature using the apparatus shown in FIGS. 1(a), (b) and FIGS. 2(a)–(d).

The input unit 1a comprises the high-input resistance voltmeter 10 for measurement of the partial pressure of carbon dioxide, and the temperature measuring circuits 11, 12, identical with those used in Experiment 1. The outputs of the voltmeter 10 and circuits 11, 12 are converted into digital signals delivered to the multiplexer 16 and then transmitted as light signals by the optical transmitting circuit 17. The light signals are sent to the interface 2 on a time-sharing basis via the optical fiber cable 4. The interface 2 inputs the data to the processing unit 3. In the experiment, a GP-IB interface was used as the interface 2. A personal computer (the NEC PC-9801VM4, manufactured by Nippon Electric Co.) was used as the processing unit 3.

With the carbon dioxide electrode used in this example, the partial pressure of carbon dioxide [$pCO_2$] and electromotive force E are related by the following equation:

$$E(\text{mV}) = a_2 + b_2 \cdot T + s \cdot \log[pCO_2]$$

where $a_2$, $b_2$ and s are undetermined coefficients, E represents the measured electromotive force, and T stands for the absolute temperature. Accordingly, we may rewrite the foregoing as follows:

$$[pCO_2] \text{ (mm Hg)} = \text{anti-log}\left(\frac{E - a_2 - b_2 \cdot T}{s}\right) \quad (2)$$

If the undetermined coefficients $a_2$, $b_2$ and s are calculated, the partial pressure of carbon dioxide can be measured from a cubic equation. Accordingly, if the potential difference E of a carbon dioxide electrode in three types of solutions having a known temperature and partial pressure of carbon dioxide is measured, and if the temperature T (° C.) is measured, then the partial pressure of carbon dioxide can be obtained from the calibration equation (2).

The continuous measurement of carbon dioxide partial pressure will now be described as a specific example.

Figure 13:
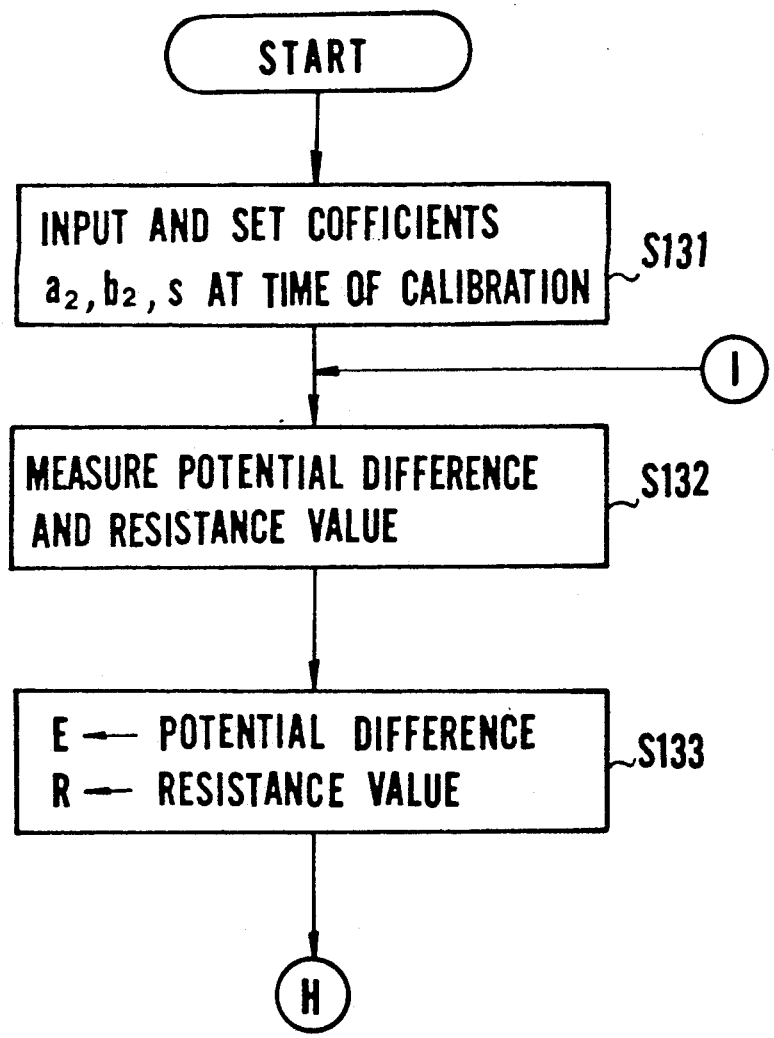
FIGS. 13(a), (b) are flow charts of a program for calculating the partial pressure of carbon dioxide.
Figure 13:
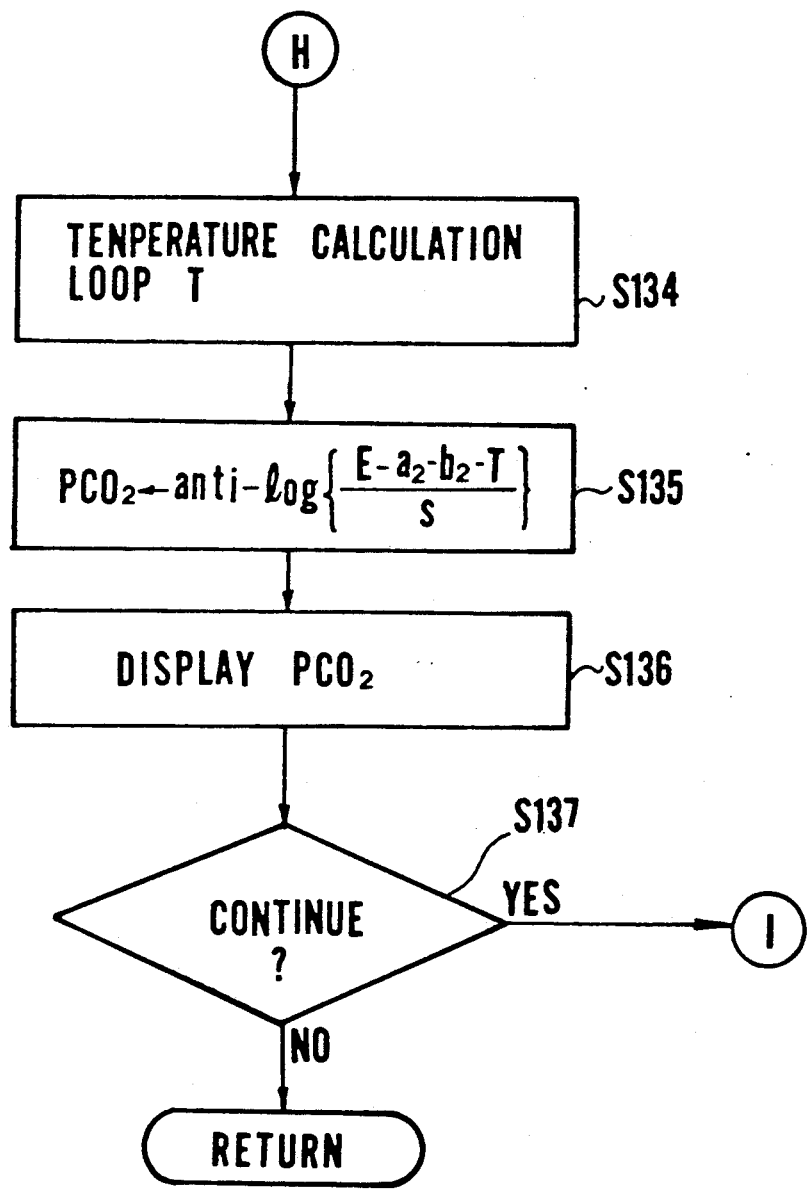

A carbon dioxide electrode and a thermister are disposed in a circulating solution (10 mM $NaHCO_3$ + 154 mM NaCl). The potential E of the carbon dioxide electrode and the temperature T of the thermister are read in by processing unit 3 through the input unit 1a, multiplexer 16, optical fiber 4 and interface 2. The partial pressure of carbon dioxide in the circulating solution is calculated from Eq. (2) in accordance with a flow chart shown in FIGS. 13(a), (b).

Coefficients $a_2$, $b_2$, s prevailing at the time of calibration are input and set at a step S131. Next, the potential difference and the resistance value from the thermister are read in through the input unit 1a, multiplexer 16, optical fiber 4 and interface 2 at a step S132, and these are stored at a step S133.

A step S134 calls for calculation of temperature T in accordance with the temperature calculation flow chart of FIG. 9(a), (b). This is followed by a step S135, $pCO_2$ is calculated from the temperature T and potential difference E using Eq. (2). The results of measurement are displayed at a step S136. It is determined at a step S137 whether measurement is to continue. If the answer here is YES, then the program returns to the step S132 and steps S132 through S137 are repeated.

Figure 11:
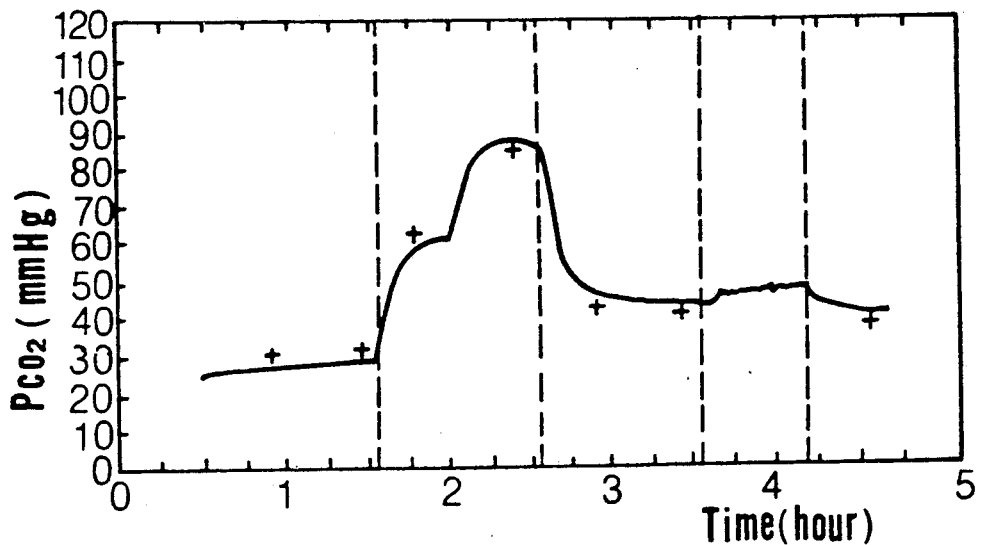
FIGS. 11(a)-(c) are graphs illustrating the results of measurement comprising temperature values, electrical potential values and temperature-compensated $CO_2$ partial pressure values (i.e. $pCO_2$ values) obtained with the biological information measurement apparatus of the embodiment.
Figure 11:
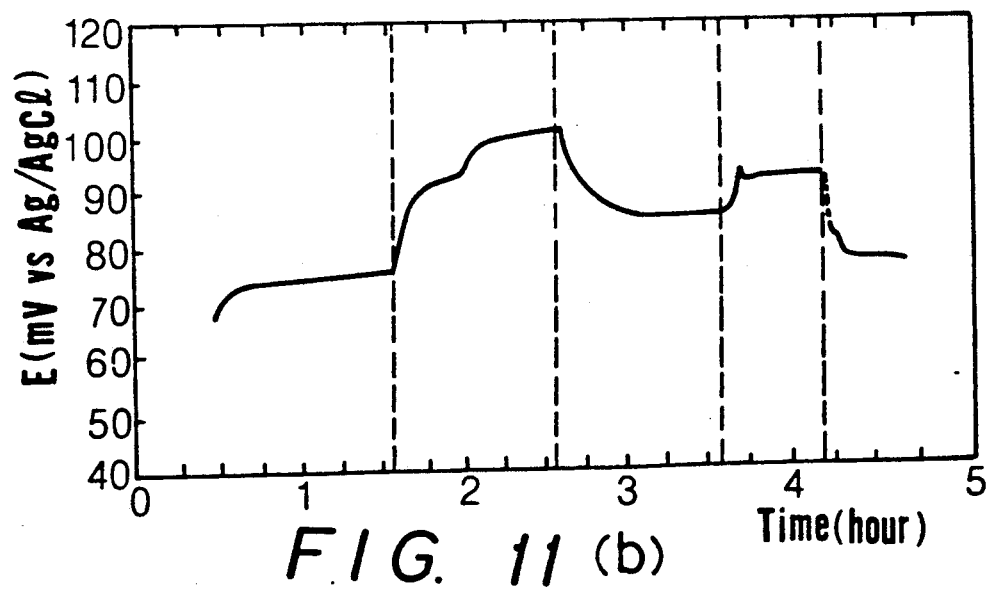
Figure 11C:
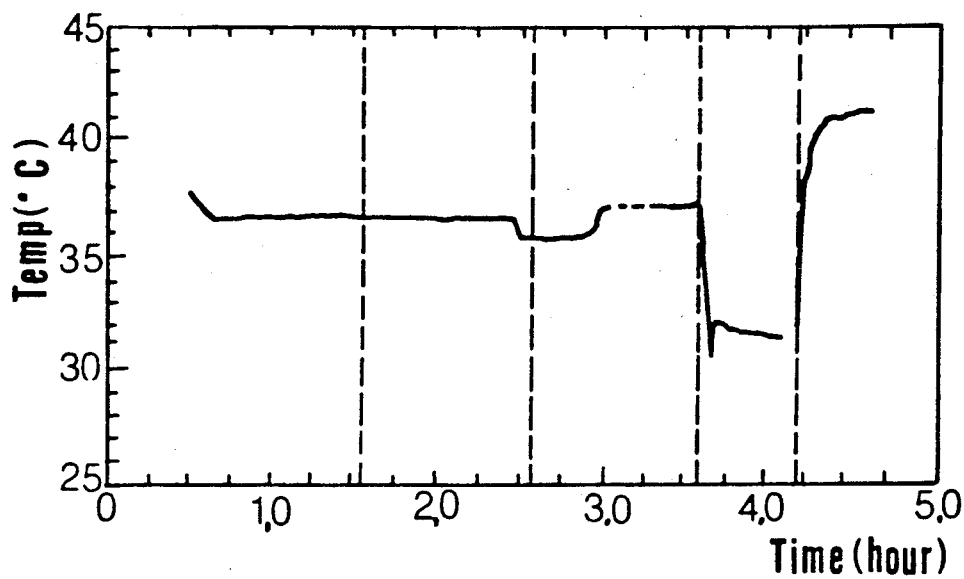

As illustrated in FIGS. 11(a) through 11(c), the results of measurement show that the value of the partial pressure of carbon dioxide can be measured accurately even if the circulating solution temperature 0 varies. The "+" marks indicate the measured values obtained by sampling the circulating solution and using a readily available carbon dioxide sensor (the ABL-30 manufactured by Radiometer).

EXPERIMENT 4

Figure 12:
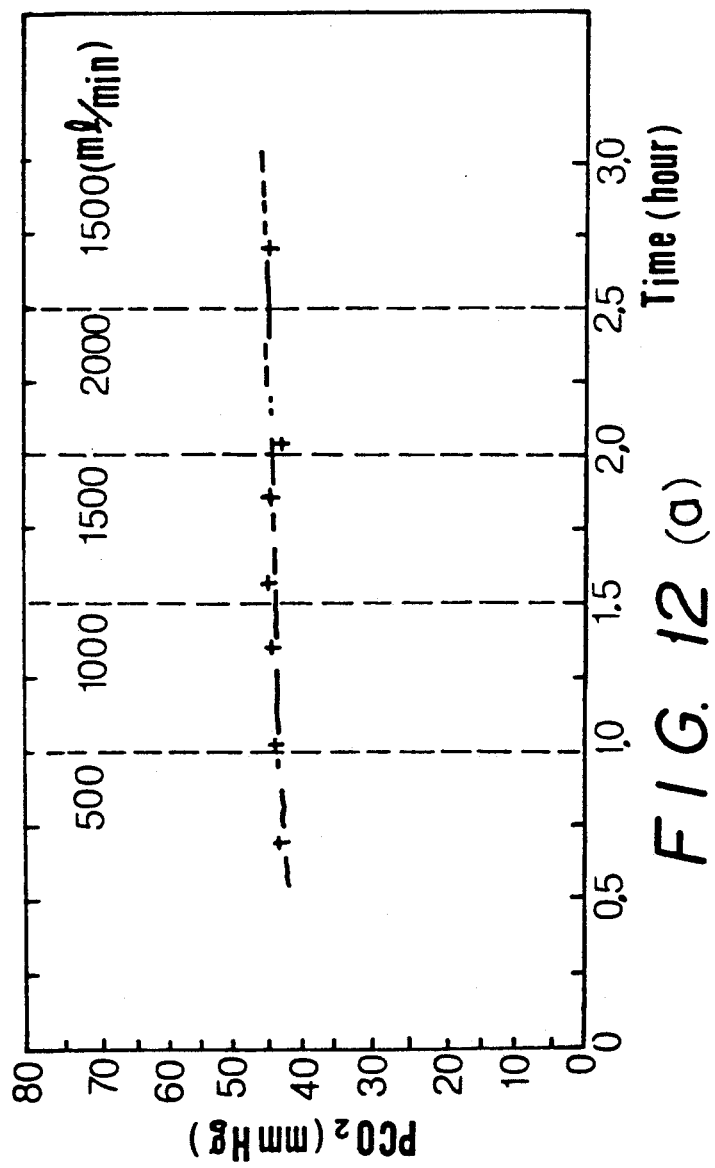
FIGS. 12(a)-(c) are graphs illustrating the results of measurement comprising temperature values, electrical potential values and temperature-compensated $CO_2$ partial pressure values (i.e. $pCO_2$ values) obtained with the biological information measurement apparatus of the embodiment for a case where a circulating liquid flowrate is varied.
Figure 12:
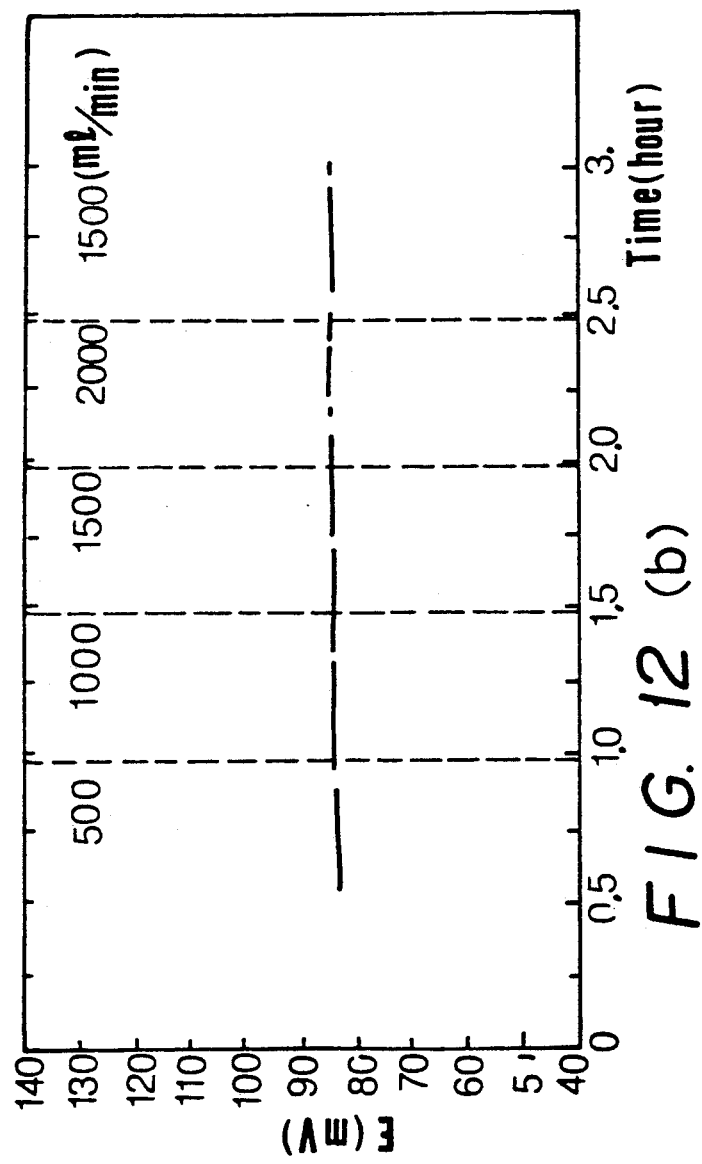
Figure 12:
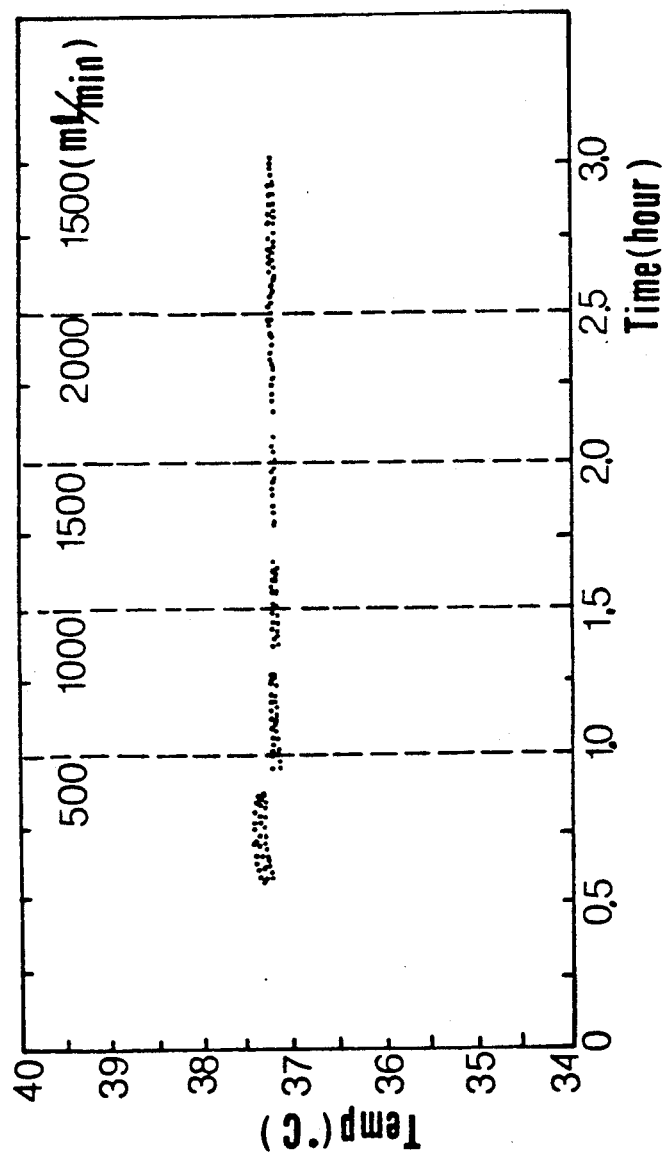

A continuous measurement was taken in the same manner as in Experiment 3 while the flowrate of the circulating solution (10 mM $NaHCo_3$ + 154 mM NaCl) was varied from 500 ml/min to 200 ml/min. As shown in FIGS. 12(a) through 12(c), the results of measurement are unaffected by the electrical noise produced by the motor of a roller pump and by variations in flowrate and temperature. Furthermore, since optical fibers are used for the data transmission, the influence of electrical external noise between the input unit 1a and interface 2 is suppressed.

EXPERIMENT 5

Temperature-compensated measurement of the partial pressure of oxygen was performed by simultaneously measuring the partial pressure of oxygen and temperature using the apparatus shown in FIGS. 1(a), (b) and FIGS. 2(a)-(d).

Figure 14:
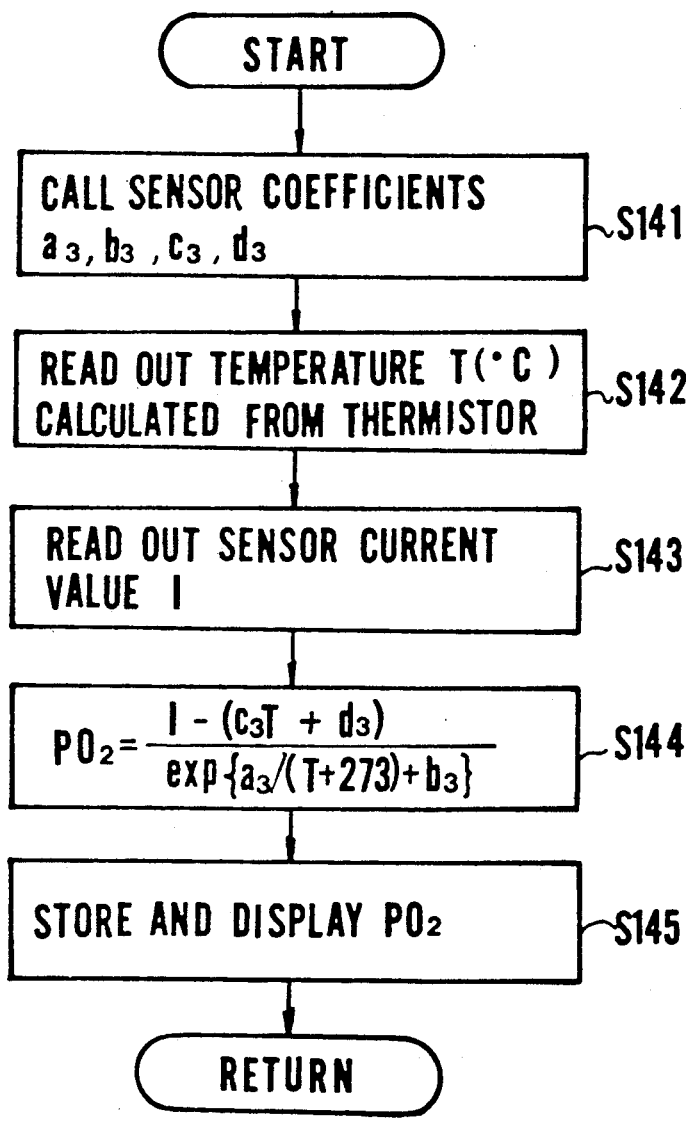
FIG. 14 is a flow chart of a program for calculating the partial pressure of oxygen.

The input unit 1b comprises the micro-ammeter 18 for measurement of the partial pressure of oxygen, and the temperature measuring circuit 19. The outputs of the ammeter 18 and circuit 19 are converted into digital signals delivered to the multiplexer 22 and then transmitted as light signals by the optical transmitting circuit 23. The light signals are sent to the interface 2 on a time-sharing basis via the optical fiber cable 4. The interface 2 inputs the data to the processing unit 3. In the experiment, a GP-IB interface was used as the interface 2. A personal computer (PC-9801VM4, manufactured by Nippon Electric Co.) was used as the processing unit 3. FIG. 14 is a flow chart illustrating the calculation of oxygen partial pressure. In the $pO_2$ sensor used in the present embodiment, oxygen partial presure $[pO_2]$ and the current value I are related by the following equation:

$$I(A) = exp\{a_3/(T+273)+b_3\{ \\ [pO_2](mmHg)+(C_3T+d_3) \quad (3)$$

where T is the temperature (° C.) prevailing at the time of measurement. Accordingly, if the current value I of the $pO_2$ sensor in four types of solutions having a known temperature and partial pressure of oxygen is measured and the undetermined coefficients $a_3$, $b_3$, $c_3$, $d_3$ of calibration equation (3) are calculated, then, by measuring the temperature T (° C.) and current value I (A), the partial pressure of oxygen can be measured very accurately without the influence of a variation in temperature.

In the flow chart of FIG. 14, the $pO_2$ sensor coefficients $a_3$, $b_3$, $c_3$, $d_3$ previously stored are called at a step S141. The temperature T (° C.) prevailing at the time of measurement and calculated from the thermister output is read out at a step S142, and the received and stored sensor current value I (A) is read out at a step S143. These values are substituted into the following equation:

$$pO_2 = \{I-(c_3T+d_3)\}/exp\{a_3/(T+273)+b_3\}$$

obtained by transforming the calibration equation (3), the value of $pO_2$ is calculated at a step S144, and the results of calculation are stored or displayed at a step S145.

Figure 15:
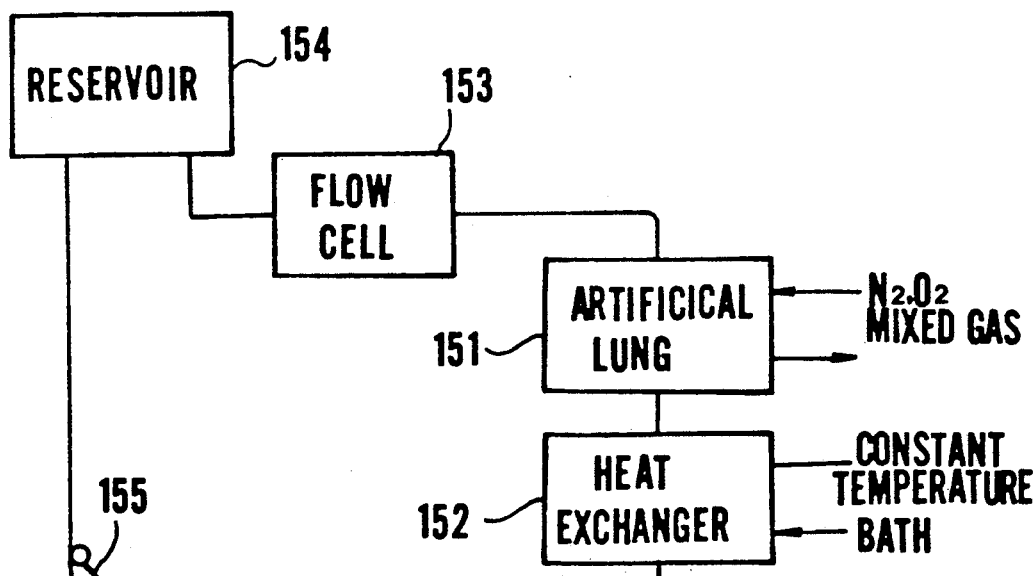
FIG. 15 is a schematic view of a circulating circuit using an experiment.

The coefficients in calibration equation (3) associated with the $pO_2$ sensor used in this example have the following values:

$a_3 = -248.3$, $b_3 = -18.97$, $c_3 = -2.28 \times 10^{-10}$
$d_3 = 2.65 \times 10^{-8}$ A circulating circuit which includes an artificial lung 151 is shown in FIG. 15. The circuit has a flow cell 153 to which a $pO_2$ sensor and thermister are attached. The current value I of the $pO_2$ sensor and the temperature T of the thermister are read into the processing unit 3 via the input unit 1b, multiplexer 22, optical fiber 4 and interface 2, and the processing unit 3 calculates the partial pressure of oxygen in the circulating fluid using Eq. (3). Numeral 152 denotes a heat exchanger, 154 a reservoir, and 155 a rotary pump.

Figure 16A:
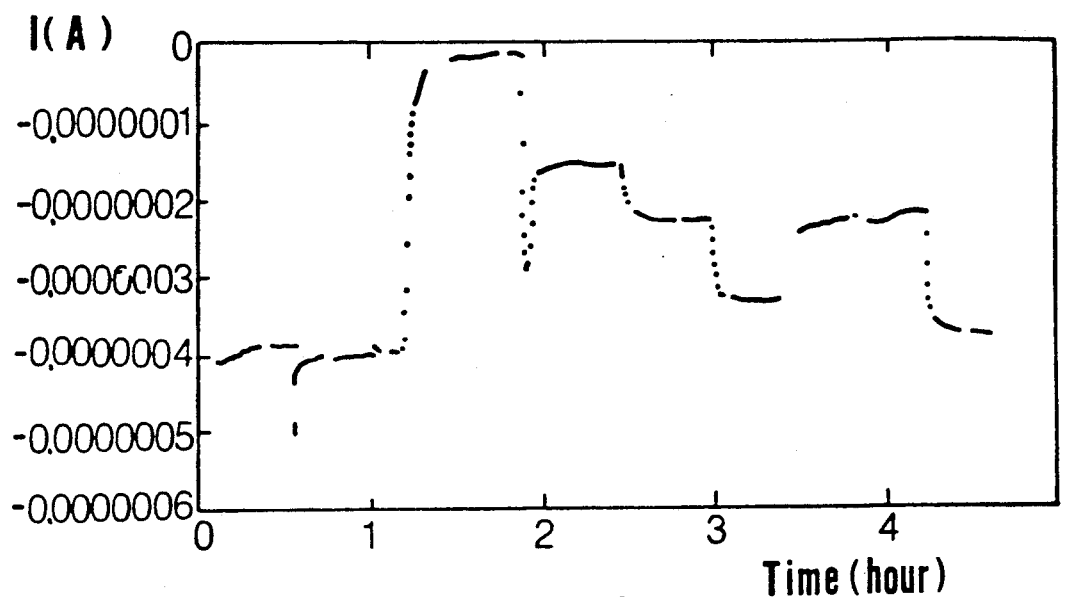
FIGS. 16(a)-(c) are views illustrating the results of measurement obtained in an experiment.
Figure 16B:
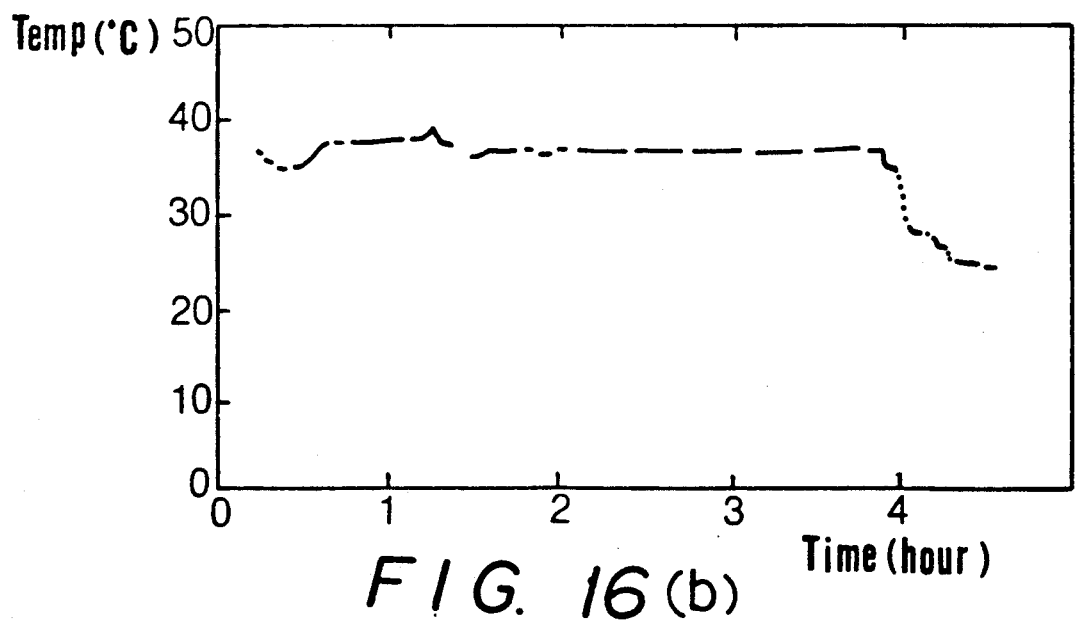
Figure 16C:
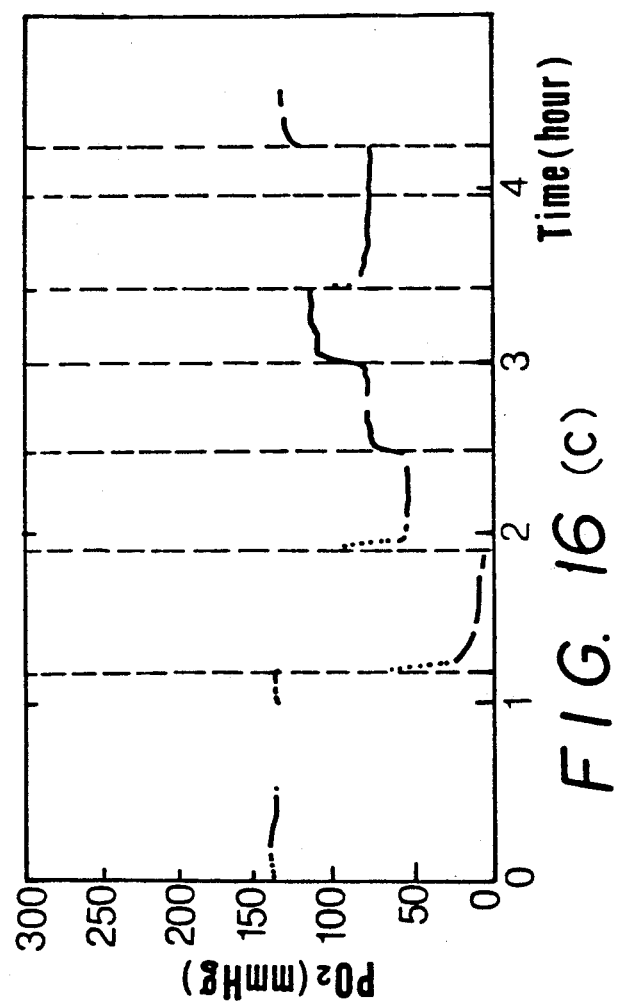

The results of measurement are shown in FIGS. 16(a), 16(b) and 16(c). FIG. 16(a) illustrates a change in the value of an $O_2$ reduction current which flows in the $pO_2$ sensor, FIG. 16(b) shows a change in thermister temperature, and FIG. 16(c) illustrates a change in the value of pO₂ calculated from values shown in FIGS. 16(a) 16(b). The solid lines in FIG. 16(c) are theoretical values of pO₂ calculated from the volume percentage of O₂ in a mixed gas of N₂ and O₂ passed through the artificial lung 151 and steam pressure. These results show that using the system of the present embodiment makes it possible sense the partial pressure of oxygen very accurately even if both temperature and pO₂ vary.

Thus, in accordance with the present embodiment as described above, the power supply of the input unit is constituted by a battery and is reduced in size. As a result, the apparatus does not require much space in the operating room or at the bedside. Since optical fiber cables are used for output, there is no danger of electric shock. The measurement section and the processing section of the apparatus are separated from each other, so that the input unit is light in weight and easy to handle.

Further, since a high-input resistance differential amplifier is used for ion, gas and enzyme sensing, stable measurements can be taken without the influence of external noise.

Since a plurality of thermometers are incorporated in the input unit so that temperature measurement and sensor temperature compensation can be carried out, highly precise measurement is performed.

Moreover, since a miniature (having a diameter of less than 1 mm) thermister is used in the temperature measurement and temperature compensation operations performed in the illustrated embodiment, thermal capacity is low and response with respect to changes in temperature is quick. In addition, since it is possible to incorporate the thermister inside an ion sensor, gas sensor or enzyme sensor, a highly precise compensation for temperature can be made.

Since the thermister uses a constant-current source in which a current of not more than 50 μA flows, self-heating of the thermister per se can be neglected. This makes possible highly accurate measurement of resistance, namely temperature. By subjecting the resistance value to high-speed repetitive processing using a computer, the resistance value can be converted into temperature rapidly and accurately even in a continuously changing system. If the temperature is used, the ion sensor or gas sensor can be subjected to a highly accurate temperature compensation.

Though the non-electrical transmission means is an optical communication system in the illustrated embodiment, in principle any means which is not influenced by electrical disturbances can be used, such as sound. Measurement is not limited to pH and gas concentration. Other biological substances can be measured by such biosensors as enzyme sensors and microbe sensors.

What is claimed is:

1. A biological information measurement apparatus comprising:
    biological information measuring means for continuously measuring electrical values corresponding to a plurality of biological information including at least one of ion-concentration and gas-concentration in body fluid and for outputting biological information signals;
    first temperature measuring means in a body with said measuring means for measuring the temperature of the body fluid adjacent said biological information measuring means and for outputting a first temperature information signal;
    transmitting means for non-electrically transmitting the biological information signals and the first temperature information signal by a time sharing method wherein it is possible to discriminate between said plurality of biological information and the first temperature information;
    converting means for converting the biological information signals and the first temperature information signal transmitted by said transmitting means into an electrical signals;
    correcting means for correcting parameters used in a calibration equation which determines said parameters through measuring said electrical values measured by said biological information measuring means under plural kinds of fluids having known ion-concentration or gas-concentration and known temperature, wherein the number of said plural kinds of fluids corresponds to the number of said parameters, each time before starting continuous measurement;
    analysis means for analyzing the biological information signals, which have been converted into the electrical signals by said converting means, in dependence upon the type of biological information, with compensation of the measured biological information including temperature-compensation by using the first temperature information signal and with said corrected parameters, which has been converted into an electrical signal by said converting means; and
    output means for outputting analytical results from said analyzing means to an external unit, the analytical results being standardized to correspond to the type of biological information.

2. The apparatus according to claim 1, wherein said transmitting means comprises optical communication means having one optical fiber cables.

3. The apparatus according to clam 1, wherein said output means comprises display means.

4. The apparatus according to claim 1, wherein said measuring means includes an internal power supply.

5. The apparatus according to claim 1, wherein said measuring means includes a differential amplifier as means for measuring electromotive force, said amplifier having a high input resistance.

6. The apparatus according to claim 1, further comprising second temperature measuring means for measuring the temperature of said biological information measuring means and for outputting a second temperature information signal in order to temperature-compensate said biological information measuring means.

7. The apparatus according to claim 1, further comprising temperature computing means for computing a temperature through a convergency technique by using process loop from said first temperature information signal which has been converted into the electrical signal by said converting means, said analysis means analyzes the biological information signal with temperature-compensation by using said computed temperature.

8. The apparatus according to claim 1, wherein said transmitting means comprises optical communication means having a plurality of optical fiber cables.

9. The apparatus according to claim 1, wherein said output means comprises memory means.

* * * * *